United States Patent
Morton et al.

[11] Patent Number: 6,117,421
[45] Date of Patent: Sep. 12, 2000

[54] METHOD FOR PROMOTING CELL GROWTH AND IMMUNOSUPPRESSION USING CHAPERONIN

[75] Inventors: Halle Morton, Coorparoo; Alice Christina Cavanagh, Ashgrove, both of Australia

[73] Assignee: The University of Queensland, Queensland, Australia

[21] Appl. No.: 08/654,575

[22] Filed: May 29, 1996

Related U.S. Application Data

[63] Continuation of application No. PCT/AU94/00740, Nov. 30, 1994.

[30] Foreign Application Priority Data

Nov. 30, 1993 [AU] Australia .................................. PM2705
Sep. 16, 1994 [AU] Australia .................................. PM8234

[51] Int. Cl.[7] .................... A61K 31/74; A61K 32/785; A61K 39/00; G01N 33/564
[52] U.S. Cl. .................... 424/78.06; 424/78.05; 424/184.1; 424/185.1; 424/190.1; 424/192.1; 424/198.1; 424/810
[58] Field of Search .................... 424/78.05, 184.1, 424/185.1, 190.1, 192.1, 198.1, 810

[56] References Cited

FOREIGN PATENT DOCUMENTS

88/04779 6/1988 WIPO .

OTHER PUBLICATIONS

Ragno et al., "A Synthetic 10KD Heat Shock Protein (HSPTO) From Mycobacteriam Tuberculosis Modulates Adjuvant Arthritis," Clin. Exp. Immunol. 103:384–390, 1996.

Rolfe et al., "Early Pregnancy Factor is an Immunosuppressant Contaminant of Commercial Preparations of HCG," Clin. Exp. Immunol. 51: 45–52, 1983.

Rolfe et al., "Identification of Two Suppressor Factors Induced by Early Pregnancy Factor," Clin. Exp. Immunol. 73:219–225, 1988.

Burgess et al., "Possible Dissociation of . . . Activities of . . . Acidic Fibroblast Growth–Factor–1 . . . by Site–Directed Mutagenesis of a Single Lysine Residue," J. Biol. Chem. III:2129–2138, 1990.

Chan et al., "Sequence & Structural Homologies Between M.Tuberculosis Chapesonin 10 and the MHC Class 1/11 Peptide Banding Cleft," Biochem. Biophys. Res. Comm. 211 (1): 14–20, 1995.

Lazar et al., "Transforming Growth Factor L: Mutation of Aspartic Acid 47 and Leucine 48 Results in Different Biological Activities," Mol. Cell. Biol. 8(3): 1247–1252, 1988.

Noonan et al., "Early Pregnancy Factor is Immunosuppressive," Nature 278: 649–651, 1979.

Cavanagh et al., "The Purification of Early–Pregnancy Factor to Homogeneity From Human Platelets and Identification As Chaperonin 10", Eur. J. Biochem., vol. 22:551–560, (1994).

Quinn et al., "Early Pregnancy Factor In Liver Regeneration After Partial Hepatectomy In Rats: Relationship With Chaperonin 10", Hepatology, vol. 20:1294–1302, (1994).

(List continued on next page.)

*Primary Examiner*—James C. Housel
*Assistant Examiner*—Ja-Na A. Hines
*Attorney, Agent, or Firm*—Foley & Lardner

[57] ABSTRACT

A process for the detection of cpn10 in serum or other biological fluids including the steps of (i) raising antibody to cpn10; (ii) reacting said antibody with a sample of biological fluid suspected of containing cpn10; and (iii) detecting the presence of cpn10 in said sample by a signal amplification resulting from production of a cpn10-antibody complex. There is also provided a process for promotion of cell growth or immunosuppression including the step of administration of cpn10 to a mammalian subject. There is also provided recombinant cpn10.

15 Claims, 20 Drawing Sheets

OTHER PUBLICATIONS

Quinn et al., "Monoclonal Antibodies To Early Pregnancy Factor Perturb Tumour Cell Growth", *Clin. exp. Immunol.*, vol. 80:100–108, (1990).

Quinn et al., "Effect of Monoclonal Antibodies to Early Pregnancy Factor (EPF) On The Vivo Growth of Transplantable Murine Tumours", *Cancer Immunol. Immunother*, vol. 34:265–271, (1992).

Hartman et al., "Identification of A Mammalian 1–kDa Heat Shock Protein, A Mitochondrial Chaperonin 10 Homologue Essential For Assisted Folding of Trimeric Ornithine Transcarbamoylase in vivo", *Proc. Natl. Acad. Sci. USA*, vol. 89:3394–3398, (1992).

Dickson et al., "Cloning, Expression, and Purification Of A Functional Nonacetylated Mammalian Mitochondrial Chaperonin 10", *The Journal of Biological Chemistry*, vol. 269(43):26858–26864, (1994).

Pilkington et al., "Complementary DNA Sequence of Bovine cpn10 (Hsp 10), A Chaperone Protein From Mitochondria", *J. DNA Sequencing and Mapping*, vol. 3:291–295, (1993).

Hartman et al., "The Complete Primary Structure Of Rat Chaperonin 10 Reveals a Putative $\beta\alpha\beta$ Nucleotide–Binding Domain With Homology to $p21^{res}$", *Biochimica et Biophysica Acta*, vol. 1164:219–22, (1993).

Chen et al., "Isolation, Sequence Analysis And Characterization Of A cDNA Encoding Human Chaperonin 10", *Biochimica et Biophysica Acta*, 1291:189–190, (1994).

Monzini et al., "Identification And Cloning of Human Chaperonin 10 Homologue", *Biochimica et Biophysica Acta*, vol. 1281:478–480, (1994).

Ryan et al., "Isolatin Of A cDNA Clone Specifying Rat Chaperonin 10, A Stress–Inducible Mitochondrial Matrix Protein Synthesised Without A Cleavable Presequence", *FEBS Letters*, vol. 337:152–156, (1994).

Cavanagh, A.C. et al., "Relationship between early pregnancy factor, mouse embryo–conditioned medium and platelet–activating factor", Journal of Reproduction & Fertility, 93:355–365, 1991.

Coulam, C.B. et al., "Evaluation of Immunological Infertility," American Journal of Reproductive Immunology, 27:130–135, 1992.

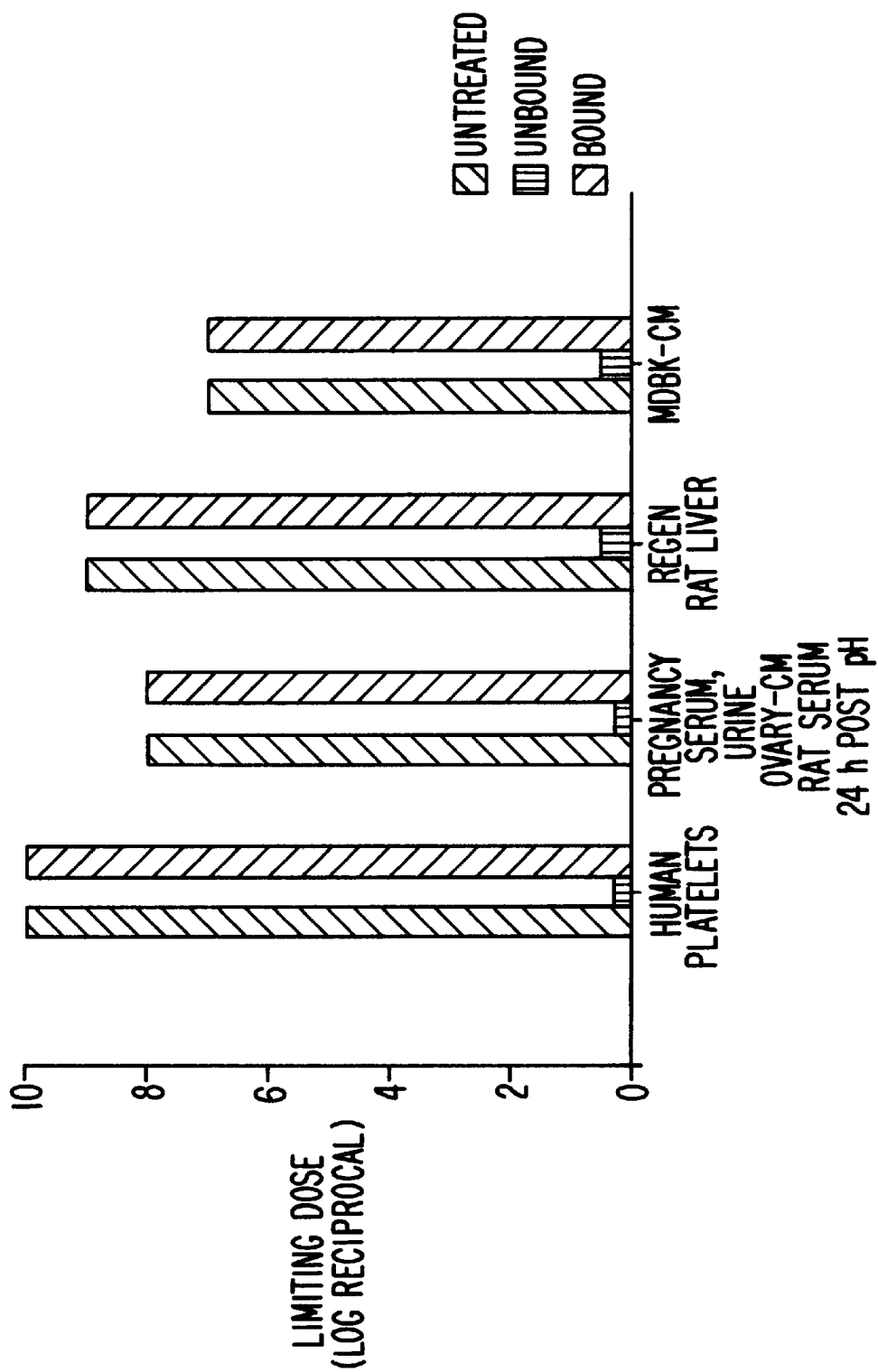

FIG. 2c

|  | | | | | |
|---|---|---|---|---|---|
| Human EPF | | KFLP | LFDRVLVE | KGGI | KV |
| Human EPF | | | LFDRVLVERS | AAETVTKGGI | KSQGKV |
| Rat cpn10 | AC-(AQAGF)RKFLP | | | MLPEKXQG | LXATVVAVGS |
| | | | | MLPEKSQGKV | LQATVVAVGX |
| | 10 | 20 | 30 | 40 | LQATVVAVGS |
| | | | | | 50 |
| Human EPF | GSK | | EYGGTKV | VXXXDXFLF | RDGDILGKYV D |
| Human EPF | GX | KV | LLPEYGGT | | |
| Rat cpn10 | GGKGKGGEIQ | PVXXKXGXXV | LLPEYGGTKV | KV | RDGDILGKYV D |
| | 60 | 70 | 80 | VLDDKDYFLF | |
| | | | | VLDDKDYFLF | RDGDILGKYV D |
| | | | | 90 | 100 |

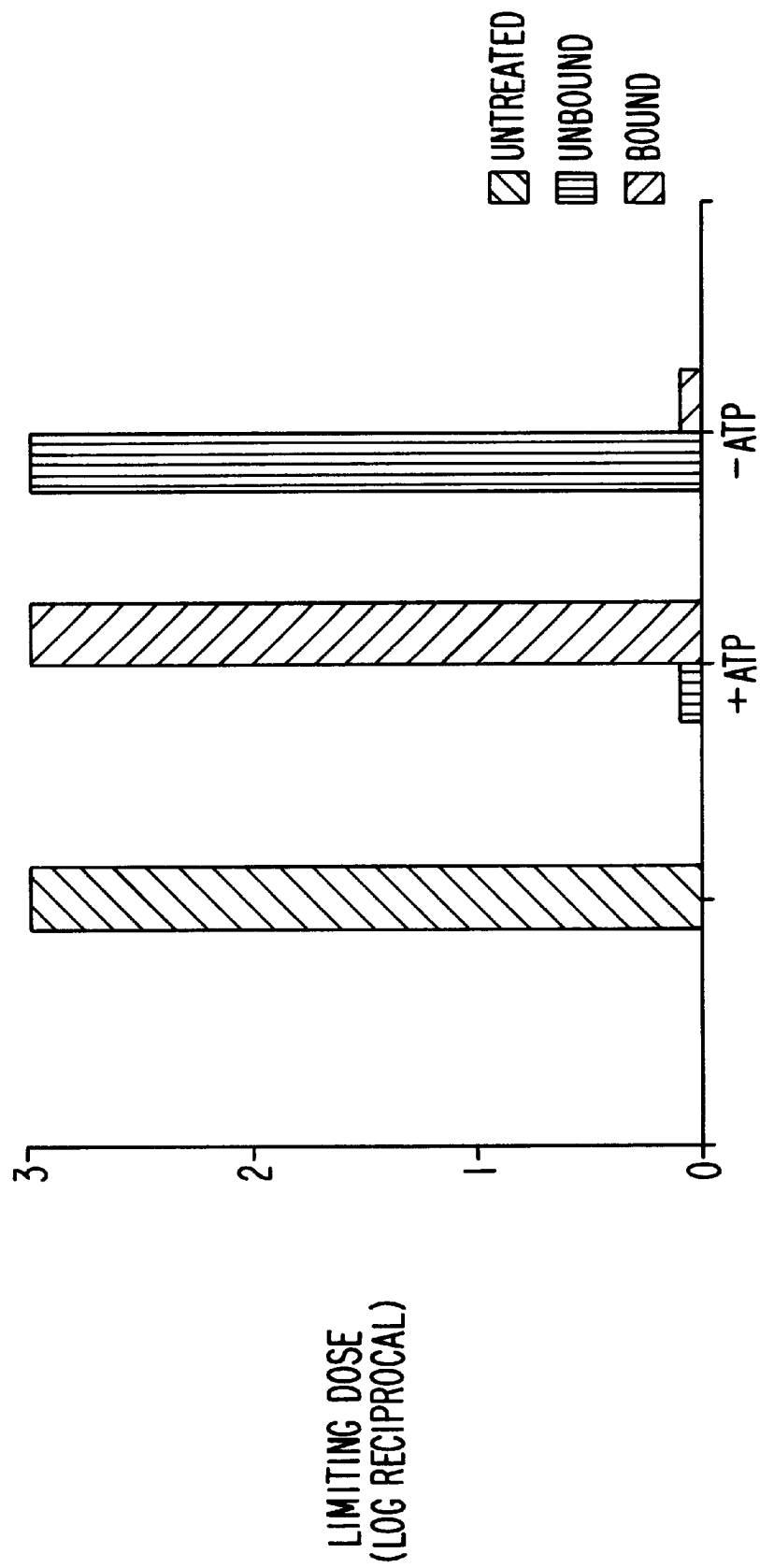

METHOD FOR PROMOTING CELL GROWTH AND IMMUNOSUPPRESSION USING CHAPERONIN

This application is a continuation application of PCT/AU94/00740, filed Nov. 30, 1994.

FIELD OF THE INVENTION

This invention relates to chaperonin 10 otherwise known as cpn10.

BACKGROUND OF THE INVENTION

Chaperonins belong to a wider class of molecular chaperones, molecules involved in post-translational folding, targeting and assembly of other proteins, but which do not themselves form part of the final assembled structure as discussed by Ellis et al., 1991, Annu. Rev. Biochem. 60 321–347. Most molecular chaperones are "heat shock" or "stress" proteins (hsp); i.e. their production is induced or increased by a variety of cellular insults (such as metabolic disruption, oxygen radicals, inflammation, infection and transformation), heat being only one of the better studies stresses as reviewed by Lindquist et al., 1988, Annu. Rev. Genet. 22 631–677. As well as these quantitative changes in specific protein levels, stress can induce the movement of constitutively produced stress proteins to different cellular compartments as referred to in the Lindquist reference mentioned above. The heat shock response is one of the most highly conserved genetic system known and the various heat shock protein families are among the most evolutionarily stable proteins in existence. As well as enabling cells to cope under adverse conditions, members of these families perform essential functions in normal cells.

There are two types of cpn molecules, cpn60 (monomeric $M_r$~60 000) and cpn10 (monomeric $M_r$~10 000). Cpn60 has been studied extensively. It has been identified in all bacteria, mitochondria and plastids examined, and a cytoplasmic form, TCP-1, has been identified in eukaryotic cells; its presence on the surface of some cells has been reported, although this has been questioned in the Ellis reference referred to above and also in van Eden, 1991, Immunol. Reviews 121 5–28. Until very recently, cpn10 had been identified only in bacteria but structural and functional equivalents have now been found in chloroplasts (Bertsch et al., 1992, Proceedings of the National Academy of Sciences USA 89 8696–8700) and in rat (Hartman et al., 1992, Proceedings of the National Academy of Sciences USA 89 3394–3398) and bovine liver mitochondria (Lubben et al., 1990, Proceedings of the National Academy of Sciences USA 87 7683–7687).

Cpn60 and cpn10 interact functionally, in the presence of ATP, to mediate protein assembly. Instances of cpn10 acting independently of cpn60 have not yet been reported but cpn60, apparently acting alone, has been implicated in quite disparate events. For example, it is an immuno-dominant target of both antibody and T-cell responses during bacterial infections but, because the protein is so highly conserved, self reactivity is generated. Healthy individuals may use this self-recognition to eliminate transformed and infected autologous cells but defects in control of such recognition may lead to autoimmune disease as discussed by van Eden, 1991, Immunol. Reviews 121 5–28. Not surprisingly, cpn60 has been associated with conditions such as rheumatoid arthritis. There is thus a growing awareness that molecular chaperones, with their capacity to bind to and alter the conformation of a wide variety of polypeptides, may occupy key roles in cellular functions other than protein biogenesis. Reference may also be made to Hartman et al., 1993, Proceedings of the National Academy of Sciences USA 90 2276–2280 which describes the stabilization of protein molecules using cpn10 and cpn60.

It can also be established that for mammalian cpn10's, there is a very close sequence homology. Thus, for example, the rat cpn10 molecule (Hartman et al., 1992, Proceedings of the National Academy of Sciences USA 80 3394–3398) has greater than 99% homology with the structure of bovine cpn10 reported in EMBL Data Base Directory under MT BTC PN10 which was submitted by J. E. Walker, MRC Lab. of Molecular Biology, Hills Road, Cambridge, UK. This has to be contrasted with bacterial cpn10's which have an average degree of homology with rat chaperonin 10 of only 34% (Hartman et al., 1992).

Early Pregnancy Factor (EPF)

EPF was first described as a pregnancy associated substance (Morton et al., 1976, Proc. R. Soc. B. 193 413–419) and its discovery created considerable interest as it enabled the detection of a potential pregnancy within 6–24 hours of fertilisation. Initially EPF was assigned a role as an immunosuppressant by virtue of its ability to release suppressor factors from lymphocytes (Rolfe et al., 1988, Clin. exp. Immunol. 73 219–225). These suppressor factors depress the delayed type hypersensitivity reaction in mice and therefore might suppress a possible maternal immune response against the antigenically alien fetus. More recent studies have shown that production of EPF is not confined to pregnancy. It is a product of primary and neoplastic cell proliferation and under these conditions acts as a growth factor (Quinn et al., 1990, Clin. exp. Immunol. 80 100–108; Cancer Immunol. Immunother, 1992, 34 265–271). EPF is also a product of platelet activation and it is proposed therefore that it may play a part in wound healing and skin repair (Cavanagh et al., 1991, Journal Reproduction and Fertility 93, 355–365).

To date, the rosette inhibition test remains the only means of detecting EPF in complex biological mixtures (Morton et al., 1976, Proc R Soc B 413–419). This assay is dependent on the original finding of Bach and Antoine, 1968, Nature (Lond) 217 658–659 that an immunosuppressive anti-lymphocyte serum (ALS) can inhibit spontaneous rosette formation in vitro between lymphocytes and heterologous red blood cells. A modification of the assay was introduced to detect EPF after it was demonstrated that lymphocytes, preincubated in EPF, give a significantly higher rosette inhibition titre (RIT) with an ALS than do lymphocytes from the same donor without EPF as described in the 1976 reference above. This test has been described in detail in the above 1976 reference as well as in Morton et al., 1987, in "In Current Topics in Developmental Biology" Vol 23 73–92, Academic Press, San Diego, but briefly it involves a cascade of events with EPF binding to lymphocytes and sequentially inducing the release of suppressor factors (Rolfe et al., 1988, Clin. exp. Immunol. 73 219–225); (Rolfe et al., 1989, Immunol. Cell Biol. 67 205–208).

In Athanasas-Platsis et al., 1989, Journal Reproduction and Fertility 87 495–502 and Athanasas-Platsis et al., 1991, Journal Reproduction and Fertility 92 443–451, there is described the production of monoclonal and polyclonal antibodies to EPF and passive immunization of pregnant mice with these antibodies which causes loss of embryonic viability. These studies established that EPF is necessary for the successful establishment of pregnancy.

In Quinn et al., 1990, Clin. exp. Immunol. 80 100–108, it is proposed that EPF is a growth regulated product of cultured tumour and transformed cells. These cells are also dependent upon EPF for continued growth i.e. EPF acts in an autocrine mode.

It has been established that EPF plays a role in promoting tumour growth since the growth of tumour cells can be significantly retarded by anti-EPF mAbs. In addition this reference suggests that hybridomas producing high affinity anti-EPF antibodies may be inherently unstable.

In Quinn et al., 1992, Cancer Immunol. Immunother, 34 265–271, there is also described the effect of monoclonal antibodies (mAbs) to EPF on the in vivo growth of transplantable murine tumours. The main thrust of this reference is that neutralisation of EPF retards tumour growth in vivo.

It is clear from the above Quinn et al. 1992 reference that when cancer is in the very early stage of growth, neutralisation of EPF by anti-EPF mAb will prevent its development. However, once the cancer becomes established, treatment with these mAbs will retard but not entirely destroy the tumour.

Other references in regard to the role of EPF in tumour growth include Quinn, 1991, Immunol. Cell Biol. 69 1–6 and Quinn, K. A. in a PhD thesis entitled "Early pregnancy factor: a novel factor involved in cell proliferation[11]" from the University of Queensland in Australia in 1991.

EPF is reviewed in detail by Morton et al., 1992, Early Pregnancy Factor, Seminars in Reproductive Endocrinology 10 72–82. The site and regulation of EPF production is described, followed by the purification of EPF from platelets and the relationship of the purified product to EPF derived from other sources. This review also discusses certain aspects of the bioassay for EPF (i.e. the rosette inhibition test) including monitoring purification procedures and investigating sources of production. The biological activity of EPF is discussed and possible clinical applications of EPF and its antagonists are described.

Morton et al., 1992, Reprod. Fertil Dev. 4 411–422 reviews previous publications describing the immuno suppressive and growth factor properties of EPF. The role of EPF in maintaining the pre-embryo is also discussed in this reference.

Both of the abovementioned references, which are essentially review articles, describe the preparation of purified EPF for blood platelets which included the initial sequential steps of heat extraction of the platelets, cation exchange chromatography on SP-SEPHADEX, crosslinked dextran beads C-25, affinity chromatography on Heparin-SEPHAROSE, crosslinked agarose beads CL-6B and Concanavalin-A-Sepharose 4B. The final purification of EPF was achieved by high performance hydrophobic interaction chromatography, followed by three reversed phase (RP)-HPLC steps. After the final RP-HPLC step, EPF was isolated as single UV absorbing peak coincident with biological activity, well separated from a number of minor contaminants. The biological and radioactivity of an iodinated sample of this material eluted with identical retention time when fractionated under the same conditions. When analysed by SDS-PAGE and visualised by autoradiography, the iodinated material ran as a single band of approximate Mr 10,000, again coincident with biological activity. The approximate yield of EPF by this method was 5 µg per 100 platelet units.

This demonstrates that it was necessary to use this complex purification procedure to obtain only a small amount of native EPF and thus this method could not be used on a commercial scale. In this regard, the only practical sources known for obtaining native EPF at this time were platelets and regenerating liver.

Surprisingly, in accordance with the present invention, the final fractionated EPF when subjected to sequencing as more fully described hereinafter found that the structure of native EPF corresponded to chaperonin 10 which could not have been predicted from the aforementioned prior art.

This unexpected discovery as will be apparent from the disclosure hereinafter has now been reduced to practice in that recombinant chaperonin 10 has been found to have all the biological activity previously associated with EPF and thus EPF can now be produced commercially which was not the case previously using suitable techniques for producing recombinant cpn10. It will also be apparent that EPF can now be produced synthetically.

SUMMARY OF THE INVENTION

In one aspect, the invention resides in the discovery that cpn10 is EPF and has the hitherto unknown or unsuspected properties demonstrated by EPF. The unknown or unsuspected properties of cpn10 include extracellular activities such as the ability to act as a growth factor and an immunosuppressive factor. In another aspect the invention provides one or more methods for using cpn10 to exploit the unknown or unsuspected properties of cpn10. The one or more methods includes a method of using cpn10 to promote growth and a method of using cpn10 to suppress immunological activity.

The term "cpn10" as used herein, insofar as methods of promotion of cell growth and immunosuppression are concerned, includes within its scope recombinant cpn10 as well as cpn10 which is produced synthetically. The term "cpn10" also includes eucaryotic cpn10 as well as procaryotic cpn10 inclusive of groES or derivatives of recombinant cpn10. The recombinant cpn10 may be produced by recombinant DNA technology as described hereinafter. The term also includes biological fragments.

The present invention also includes within its scope a modified recombinant cpn10 as well as derivatives and peptide fragments derived therefrom.

The invention in another aspect refers to an assay for detection of cpn10 which includes the detection of native cpn10.

BRIEF DESCRIPTION OF THE FIGURES

FIG. 1a

Purification of EPF. Heat extracted human platelets (100 units) were fractionated on SP-SEPHADEX and Heparin SEPHAROSE, then applied to a TSK-Phenyl 5PW column and eluted with a reverse salt gradient. Fractions were tested in the rosette inhibition test (based on EPF's capacity to augment the rosette inhibiting activity of an immunosuppressive antilymphocyte serum).

FIG. 1b

Active fractions (II) from (a) were fractionated by RP-HPLC-1.

FIG. 1c

Active fractions (II) from (b) were fractionated by RP-HPLC-2.

FIG. 1d

Active fractions (II) from (c) were fractionated by RP-HPLC-3.

FIG. 1e

Interaction of immobilised monoclonal anti-EPF antibody 5/341 with active fractions from (d) and equivalent fractions from human pregnancy serum, 6 d gestation (10 ml); human pregnancy urine, up to 1 month gestation (10 liter); medium conditioned by oestrous mouse ovaries (100) stimulated with prolactin and mouse embryo-conditioned medium (ovary CM); serum free medium conditioned by the bovine kidney cell line MDBK (MDBK-CM; ATCC CCL 22, 10 liter); rat serum obtained 24 h post-partial hepatectomy (post-pH, 10 ml); rat liver obtained 24 h post-pH (40 g); all fractionated as in (a) to (d). Anti-EPF bound and unbound fractions were tested in the rosette inhibition test, specificity was demonstrated by comparison with a parallel experiment using irrelevant antibody in which activity was not bound.

FIG. 2a

Figure 1A:
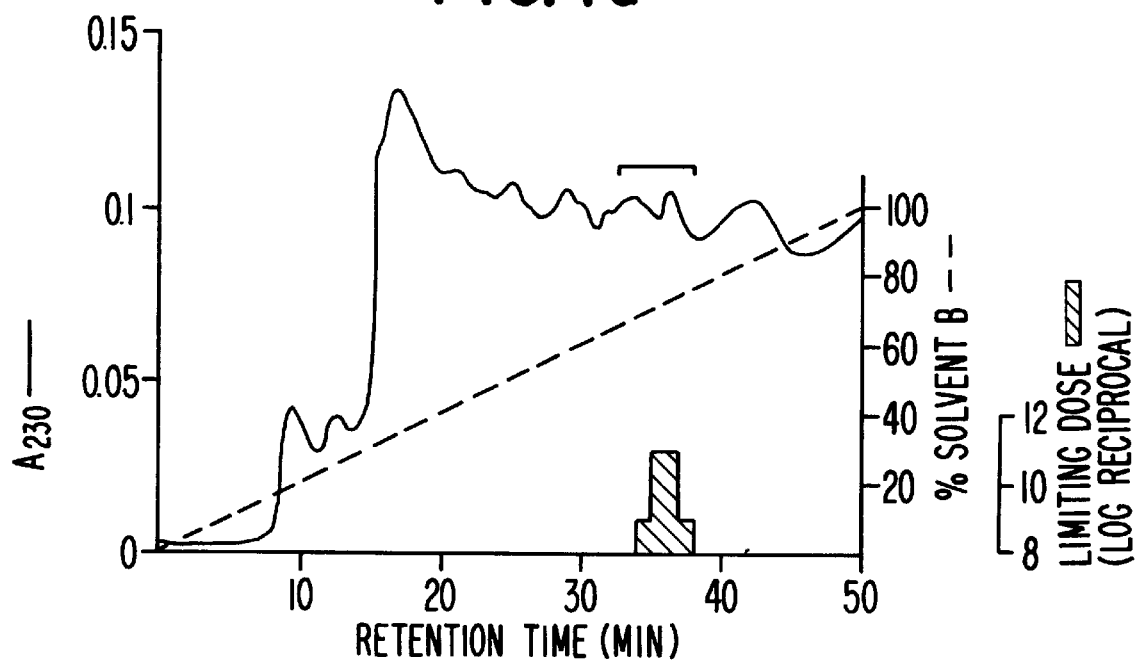

Analysis of EPF purified from 300 units human platelets as in FIG. 1A. Determination of monomeric size. Iodinated EPF was fractionated by SDS-PAGE,[29] the gel sliced (2 mm wide slices) and the distribution of radioactivity and biological activity compared. (Inset) Direct Coomassie Blue staining of the same preparation.

FIG. 2b-1

Ion-spray mass spectrum of EPF, displayed as multiply protonated molecular ions.

FIG. 2b-2

Computer reconstruction as molecular mass.

FIG. 2c

Amino-acid sequence (single letter code) of peptides derived from human EPF, compared with rat cpn10 (underlined). EPF was digested with endoproteinase lys C and endoproteinase glu C, the resultant peptides separated by RP-HPLC and sequenced. The sequence of individual fragments is shown; all except 74–101 were derived from the lys digest.

FIG. 3a

Peak fractions in the excluded volume of a TSK G3000SW gel permeation column, following application of a cpn60-EPF mixture +Mg$^{2+}$ATP, were analysed by SDS-PAGE (Schagger et al., 1987) and stained with silver (Morrissey, 1981). Left lane, +ATP; right lane –ATP. (Cpn60 is a decatetramer, M, 840 000; column exclusion limit >300 000. Higher $M_r$ bands on SDS gel are oligomeric forms of groEL).

FIG. 3b

Immobilised cpn60 was mixed with human pregnancy serum (6 d gestation) in the presence or absence of Mg$^{2+}$ATP. Unbound and bound fractions (the latter recovered from the gel by removal of ATP with EDTA) were then tested in the rosette inhibition test. Results are expressed as limiting dose, the highest dilution of sample giving a positive result in the rosette inhibition test.

FIG. 4 pRM1

FIG. 5 pRM2

FIG. 6 pRM3

FIG. 7

Preparation of antibodies to cpn10

FIG. 8

Detection of anti-cpn10 antibodies in rabbit serum by ELISA

FIG. 9

Competitive binding assay for cpn10

FIG. 10

% inhibition of antibody binding

FIG. 11

Time course of recombinant cpn10 and platelet cpn10 activity in serum of mice after injection i.p.

FIG. 12

The effect of rcpn10 on wound contraction in mice. Wounds (~45 mm$^2$) were created in mice, 1 μg rcpn10 or control solutions (5 μl) applied topically × 2 daily and the size of wound area on groups of mice measured at times indicated (means±SD); d 0, n=10 d 1–d 3, n=3, d 4–d 7, n=2*p<0.05 compared with buffer control group.

FIG. 13

Effect of the treatment regimen on development of EAE in rats.

FIG. 14

Effect of cpn10 on development of EAE in rats.

FIG. 15

Effect of cpn10 on development of EAE in rats.

DETAILED DESCRIPTION OF THE PREFERRED EMBODIMENTS

The present invention includes within its scope the following.

Assay For cpn10

The detection of cpn10 in serum or other biological fluids using monoclonal or polyclonal antibodies against recombinant or synthetic cpn10or against modifications or fragments thereof alone or in combination with each other or with cpn60 (in the presence of ATP or other nucleotide triphosphates) for the purpose of:

(a) pregnancy diagnosis in any mammalian species;
(b) monitoring embryonic well-being in "at-risk" pregnancies;
(c) diagnosis of tumours; and
(d) monitoring patients after surgical removal of tumours.

Treatment With CPM10

The use of recombinant cpn10 as a growth factor or immunosuppressant in the treatment of:

(a) skin or organ grafts;
(b) wound healing, tissue repair or regeneration of tissue;
(c) autoimmune disease;
(d) infertility/miscarriage;
(e) allergic disease; and
(f) inflammatory conditions.

Experimental

Purification of cpn10

(a) Purification of Human EPF from Human Blood Platelets (FIG. 1a, 1b, 1c, 1d)

Extraction

Platelet concentrates (from the Blood Bank), up to 7 days clinically outdated, were washed with Tyrodes buffer, following the techniques described in Methods in Enzymology, 1989, 169 7–11, snap frozen in liquid N$_2$ and stored at −70° C.

Immediately prior to purification, approximately 100 washed platelet units were thawed in a boiling water bath, then held at 75–85° C for 15 min with continuous, gentle stirring. After cooling on ice, cellular debris was removed by centrifugation (8000 g, 20 min, 4° C.) and the pellet extracted twice by homogenisation in 0.05 M-acetic acid/0.1 M-NaCl/0.1 mg/ml sodium azide pH 3.0 followed by centrifugation (8 000 g, 15 min 4° C.). The three supernatants were pooled giving a total extract volume of 500–600ml.

Ion-Exchange Chromatography

This extract from 100 platelet units was adjusted to pH 3.0 with conc. HCl and stirred gently, overnight, 4° C., with 250ml SP-SEPHADEX, crosslinked dextran beads C-25 (Pharmacia-LKB), previously swollen and equilibrated with 0.05 M-acetic acid/0.1 M-NaClpH 3.0. The gel was then packed into a column washed with 20 vol of the same buffer and eluted with 5 vol 0.5 M-sodium phosphate buffer/0.05 M-NaClpH 7.5. The gel was then discarded.

Affinity Chromatography

The SP-SEPHADEX, crosslinked dextran beads; eluate was adjusted to pH 6.3–6.4 with conc. HCl and applied to a column of Heparin-SEPHAROSE, crosslinked agarose beads CL-6B (2.5×7.5 cm; Pharmacia-LKB) previously equilibrated with 0.05 M-sodium phosphate buffer 0.05 M-NaCl pH 6.3. The column was then washed with 5 vol of the same buffer and eluted with 5 vol 0.05 M-Tris-HCl/5 mM-CaCl$_2$/0.2 M-NaCl pH 7.5, applied in the reverse direction to that used for sample application.

High Performance hydrophobic Interaction Chromatography (HIC-h.p.l.c.)

Solid $(NH_4)_2SO_4$ was added to the Heparin-SEPHAROSE, crosslinked agarose beads eluate to a final concentration of 2 M and, after passage through an 0.45 μm filter, the sample was pumped through a dedicated solvent line onto a TSK Phenyl 5PW column (7.5×75 mm, Pharmacia-LKB), previously equilibrated with 0.1 M-Tris-HCl pH 7.0/5mM CaCl$_2$/2 M-$(NH_4)_2SO_4$. The column was washed with 10 vol of the same buffer and eluted with a 50 min linear Gradient from this buffer to 0.1 M-Tris-HCl pH 7.015 mM-CaCl$_2$/10% acetonitrile. (FIG. 1a)

RP-h.p.l.c.

Figure 1B:
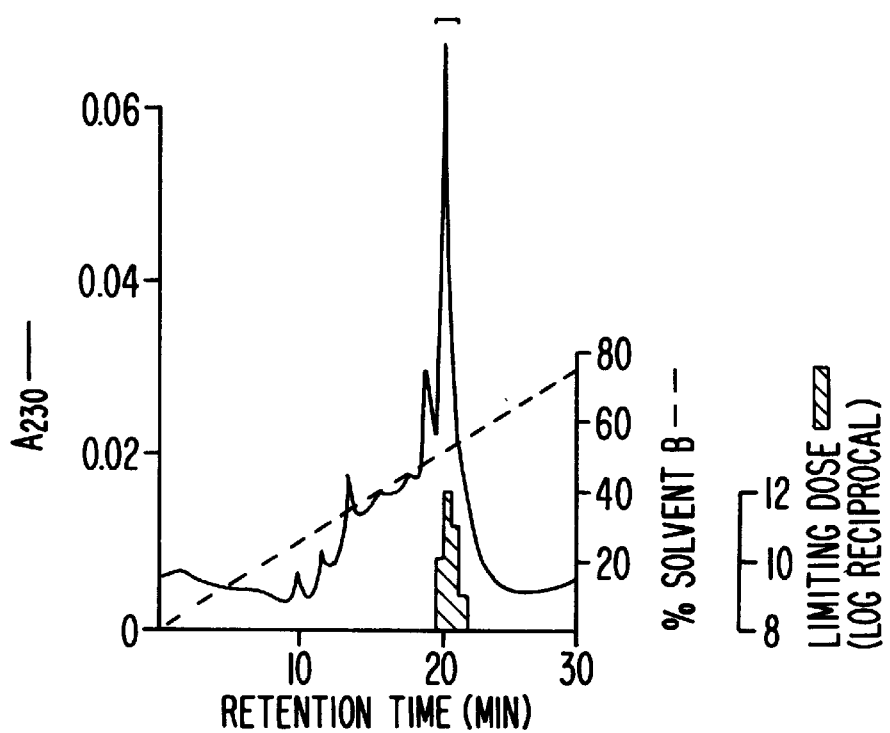

Active HIC-h.p.l.c. fractions were pooled, then fractionated on a C$_3$ column (Ultrapore RPSC. Beckman Instruments) using a solvent system consisting of A, 0.04 M Tris/HCl pH 7.0/5 mM-CaCl$_2$ and B, 0.04 M-Tris/HCl pH 7.0/5 mM-CaCl$_2$/80% (v/v) acetonitrile. The column was equilibrated with Solvent A prior to sample application, after which it was washed with 5 vol solvent A and eluted with a 30 min linear gradient from this solvent to 75% solvent B. (FIG. 1b)

RP-h.p.l.c.2

Figure 1C:
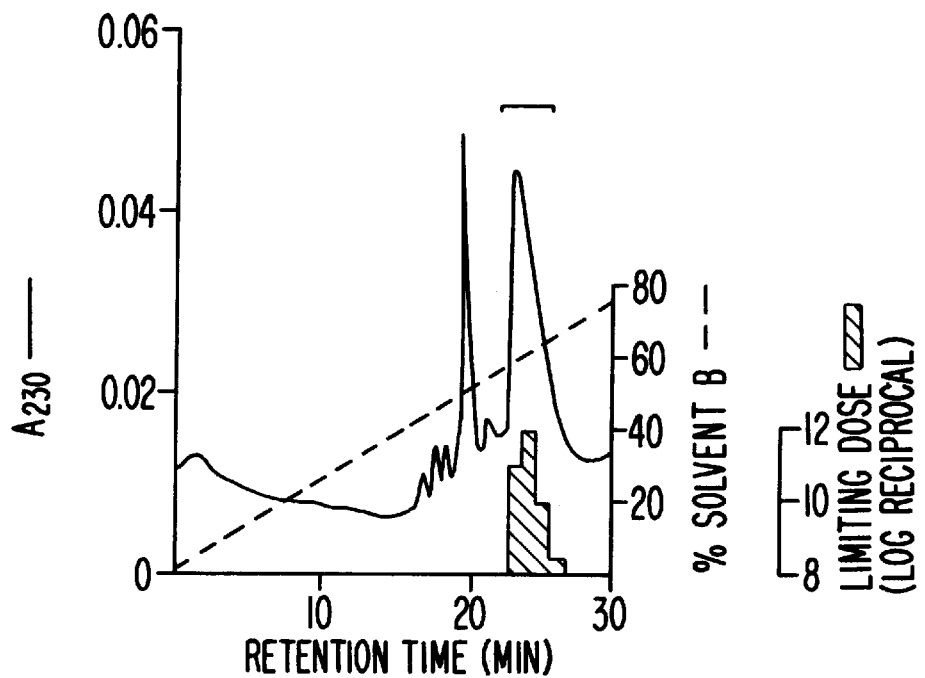

Active fractions from RP-h.p.l.c.-1 of several 100 unit platelet preparations were pooled, EDTA and DTT added to a final concentration of 20mM and 1mM respectively and the mixture allowed to stand for 0.5–1 h, 4° C. Following dilution with 2 vol solvent A, it was applied to a C$_3$ column, dedicated to this and subsequent steps, and fractionated as described for RP-h.p.l.c.-1, but omitting CaCl$_2$. (FIG. 1c)

Rph.p.l.c.3

Figure 1D:
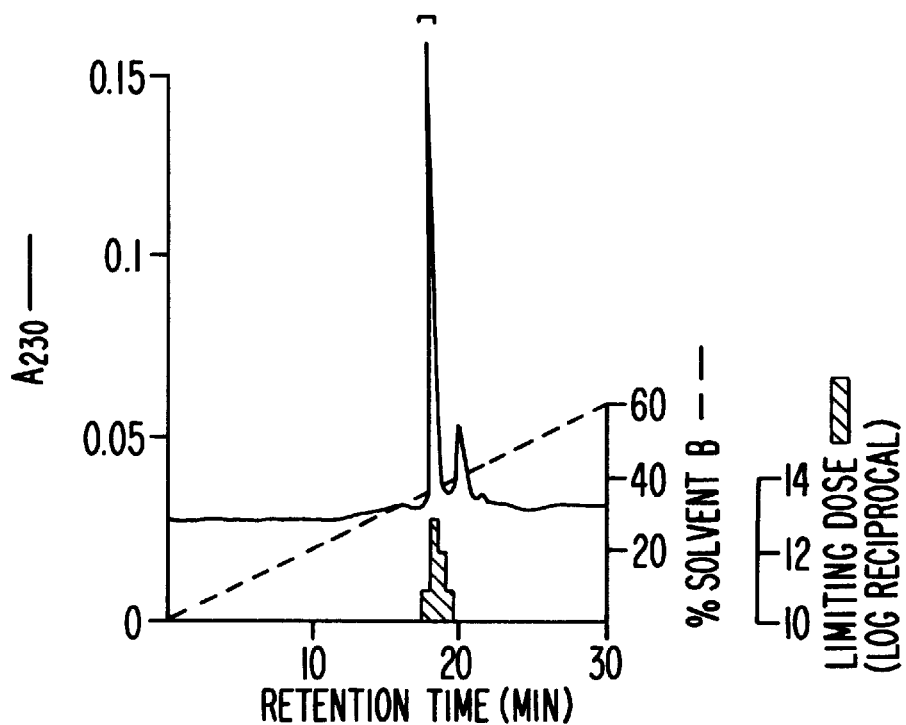

Active fractions from RP-h.p.l.c.-2 were pooled, trifluoroacetic acid (TFA) added to a final concentration of 0.1% and, following dilution with 2 vol 0.1% TFA, the mixture was applied to the C$_3$ column, which had been equilibrated previously with 0.1% TFA. The column was then eluted with a 30 min linear gradient from this solvent to 60% (v/v) acetonitrile/0. 1% TFA, followed by a 3 min linear gradient to 90% (v/v) acetonitrile/0. 1% TFA. Active fractions were pooled. (FIG. 1d)

One unit represents platelets from a single blood donation which is approximately 500 ml. The "active fractions" were fractions active in the rosette inhibition test.

Purification of EPF from other sources

EPF has been purified from various sources as discussed in Cavanagh & Morton, 1994, Eur. J. Biochem. 222 551–560; Quinn et al., 1994, Hepatology 20 No 5 1294–1302.

In all instances, biological activity followed the same pattern throughout the complex purification scheme described above for human platelets. Furthermore the final active fraction from all sources was bound specifically by an immobilised monoclonal anti-EPF and could be recovered virtually quantitatively (see FIG. 1e).

These studies are important for several reasons:

A. The biochemical and immunological similarity observed with all these materials provides strong evidence that the bioassay is detecting a single substance or closely related family of substances acting in diverse biological situations.

B. The active agents purified from all of these materials are from several to many orders of magnitude more potent than virtually all of the substances previously reported to be EPF. This confirms our surmise, based on detailed analysis of the EPF bioassay as discussed above, that activity associated with most putative EPF preparations must reflect the presence of a very minor contaminant.

C. The only source materials providing sufficient EPF to study at the protein (as opposed to activity) level were platelets and regenerating liver, yielding, respectively, an average of 15 μg per 100 units (equivalent to ~50 liter blood) and 5 μg per 40 g tissue (liver remnant from 6 rats). It is immediately apparent that far more EPF is present within the cell than appears in the extracellular space; nevertheless, accumulated knowledge of the biology of EPF (reviewed recently in the abovementioned Morton et al. 1992 reference) indicates that this extracellular appearance is not fortuitous.

Figure 2A:
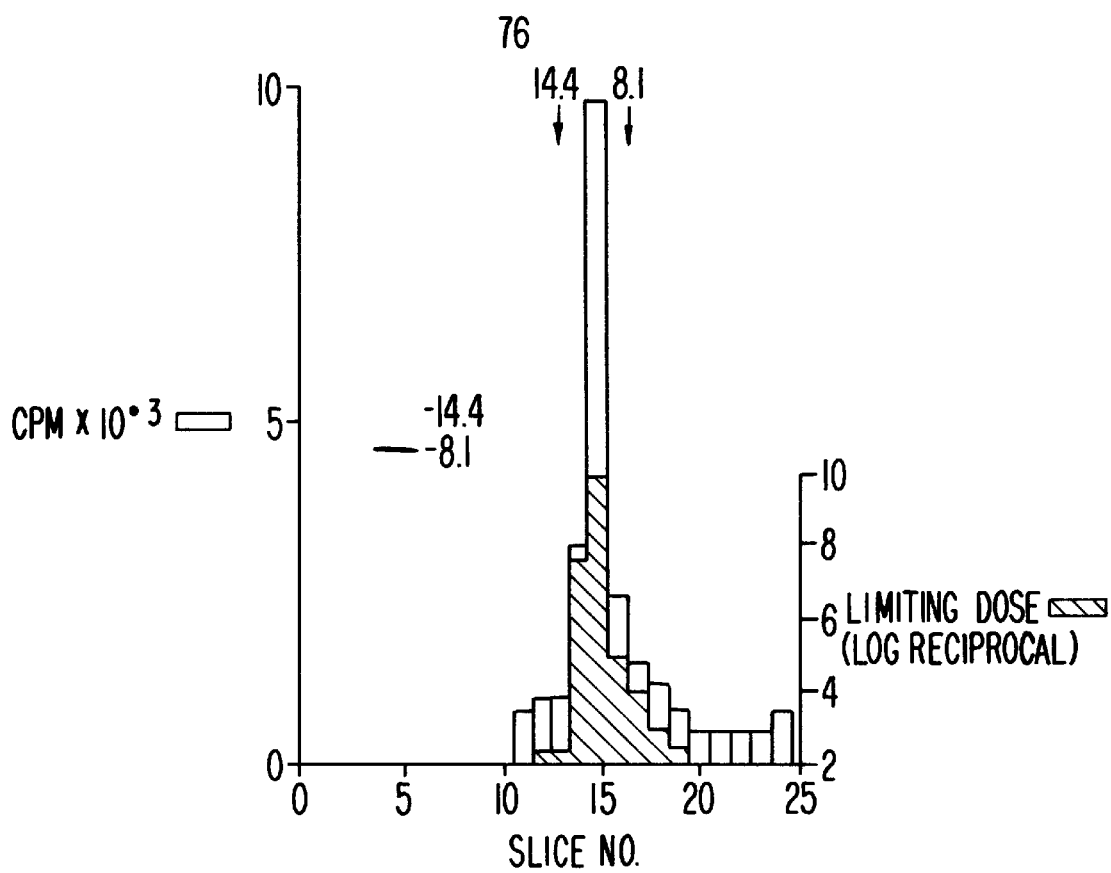
Figures 1, 2, 2B:
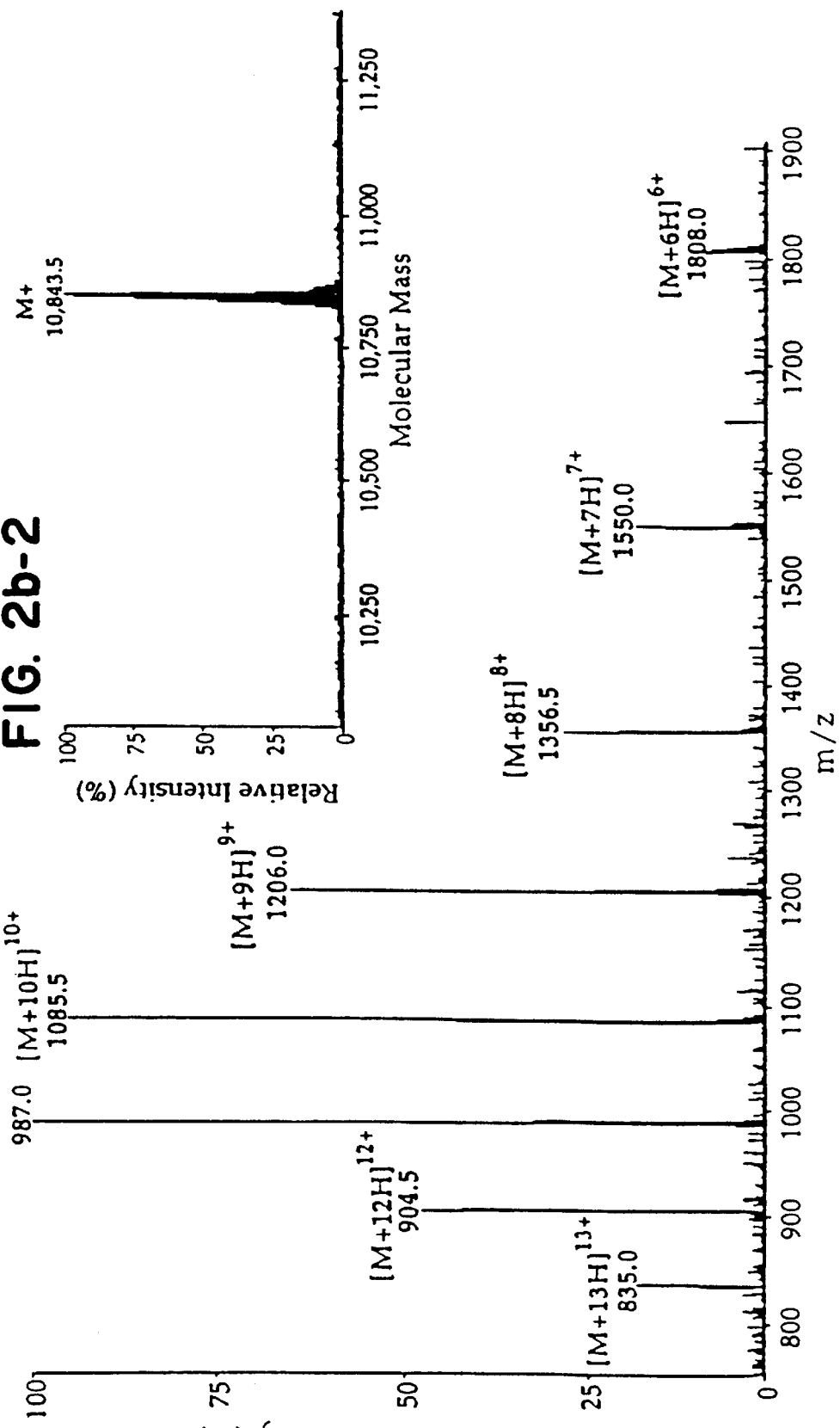

Human platelet-derived EPF, being most abundant, has been studied in some detail. On SDS-PAGE, it ran as a single band of Mr approx, 8.500, coincident with biological activity (see FIG. 2a); EPF from regenerating rat liver exhibited identical behaviour. Mass spectometry of the platelet material provided an accurate and precise determination of molecular mass 10 843.5±2 Da, along with definitive evidence of the high degree of homogeneity of the preparation (see FIG. 2b). Following attempts at Edman degradation, which indicated that the molecule is N-blocked, proteolytic cleavage of approx. 4 nmol EPF was undertaken. Resultant peptide fragments were separated by reversed-phase HPLC and subjected to sequencing by Edman degradation. Three areas of sequence containing 12 (fragment 1), 27 (fragment 2) and 33 (fragment 3) residues were found to correspond with residues 7 to 18–27–53 and 69 –101 (the C-terminus) in rat mitochondrial cpn10. In fragment 2, residue 52 was different (S in cpn10, G in rat cpn10, this change alone could account for human cpn10 being 30 Da larger than rat cpn10). All other residues were identical, consistent with the highly conserved nature of chaperonins (see FIG. 2c).

Since confirming sequence identity between EPF and cpn10 several studies of functional relationship have been performed, using rat mitochondrial cpn10 E. coli cpn10 (known as groES) and E. coli cpn60 (groEL). First it has been demonstrated that cpn10 can act as EPF. Rat cpn10 was tested in the EPF bioassay and found to be positive over the range of dilutions expected; this activity could be neutralised by monoclonal antibodies to EPF (see TABLE 1). Interestingly, E. coli cpn10, which is ~ 40% homologous with rat cpn10, exhibited no activity in the bioassay (see TABLE 1): this is consistent with the observation that E. coli conditioned medium is not active in the EPF bioassay, while medium conditioned by all mammalian cell lines tested, as well as by yeast cells is active. Cpn60 was inactive in the bioassay and had no effect upon the activity of EPF. It was then shown that EPF can act as cpn10. EPF was mixed with cpn60, in the presence or absence of ATP, and the mixture fractionated on a TSK G3000SW gel permeation column: resultant fractions were analysed by SDS-PAGE. Cpn60 is a decatetramer and elutes in the excluded volume of this column (exclusion limit 300 000). In the presence of ATP, but not in its absence, EPF also appears in this fraction, demonstrating formation of a stable complex with cpn60. This fraction was active in the EPF bioassay but the equivalent fraction from the experiment without ATP (where EPF did not associate with cpn60) was not (see FIG. 3a). Thus EPF and cpn10 activity reside in the same molecule.

Figure 3A:
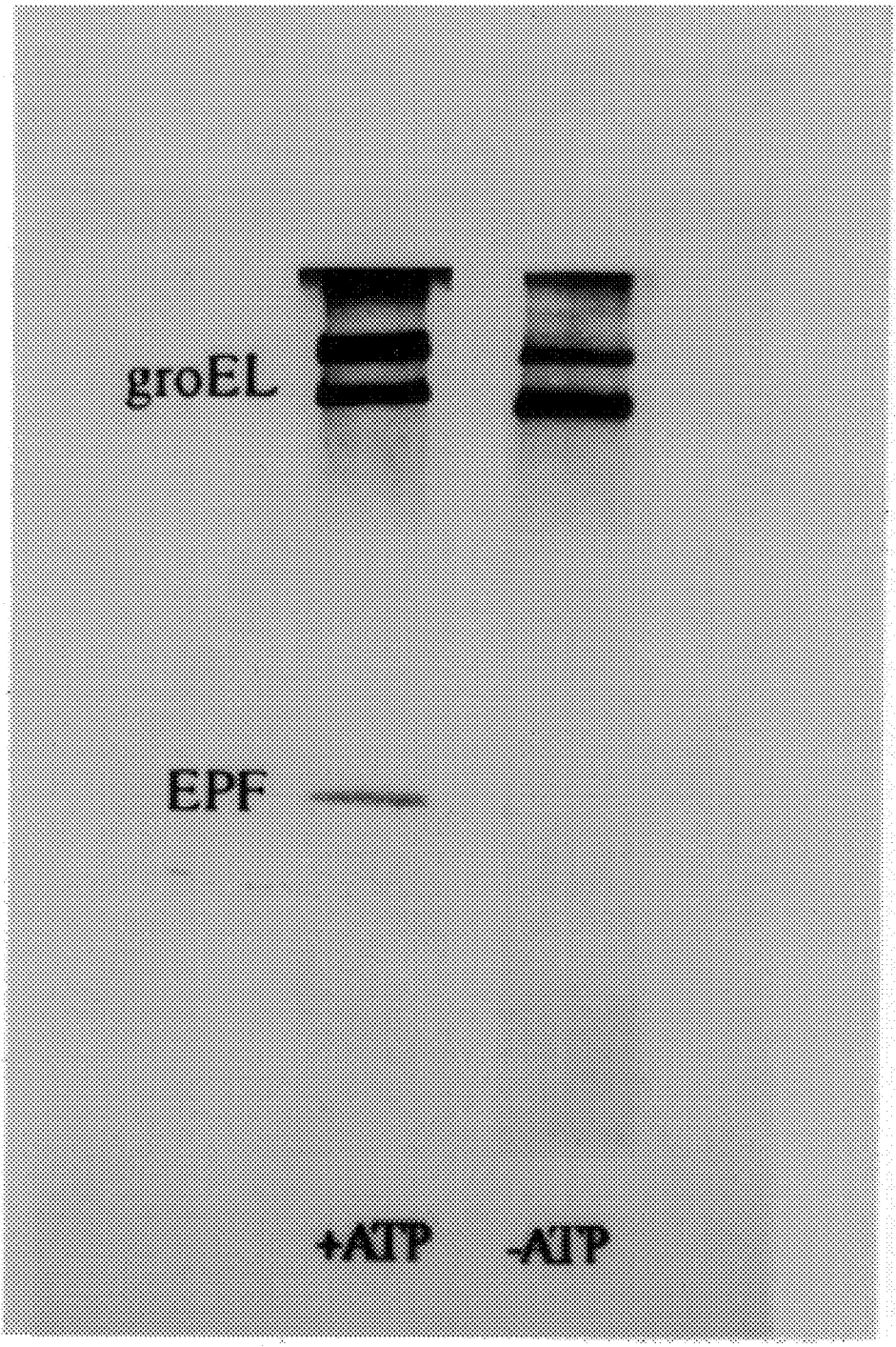

These investigations provide unequivocal evidence that platelet-derived EPF is a structural and functional homologue of cpn10the relationship between cpn10 and activity in the rosette inhibition test was then examined (FIG. 3b). In the presence, but not in the absence of ATP, immobilised cpn60 could remove all activity from the archetypal source material, pregnancy serum and activity could be recovered by removing ATP from the immobilised complex. As with the experiment described in FIG. 3a, this requirement for ATP demonstrates the specificity of the interaction between cpn60 and the active moiety; cpn10 is thus the molecular entity initiating response in the EPF bioassay.

Identification of EPF as a cpn10 has been a major step forward in research on this subject and helps to explain many of the findings that have been made to date. Criticism has been raised against claims that EPF production occurs in such a wide variety of biological situations e.g. pre- and post-implantation pregnancy, primary and tumour cell proliferation and platelet activation. In its role as a hsp (heat stress protein) following the advent of the present invention, these are all conditions in which the rapid onset of EPF production would now be expected. Functions of hsp's that are vital to the survival of cells are intracellular as shown in the Linquist et al. reference above. In contrast, the activity of EPF described to date is extracellular; for example, it appears in serum of mice within 4 to 6 hours after mating as discussed in Morton et al., 1987, Current Topics in Development Biology, Vol 23 73–92 and 4 to 8 hours after partial hepatectomy in rats as shown in the Quinn PhD thesis (1991), available from the Biological Sciences Library, University of Queensland Australia, catalogued under both author and title. We have shown that EPF can act in an autocrine mode as discussed in the Quinn et al., 1990 reference referred to above or exocrine mode as discussed in the Rolfe et al. 1988 referred to above; these are not roles previously described for hsp's.

It will also be appreciated that since the structure of EPF is now known, it can be produced in commercial quantities by any suitable technique of recombinant DNA technology.

(b) Cloning of Human cDNA Encoding cpn10 and Production of cpn10

Production for commercial use may be obtained by inserting a mammalian cpn10 gene, preferably a human cDNA cpn10 gene, into a suitable vector such as plasmids from the pGEX system, and pET system expressing the encoded mammalian cpn10 and purifying the recombinant cpn10.

| Abbreviations | |
|---|---|
| ANGIS | Australian National Genomic Information Service |
| bp | base pair |
| BSA | bovine serum albumin |
| cDNA | complementary DNA |
| cpn 10 | Chaperonin 10 |

| -continued | |
|---|---|
| Abbreviations | |
| DNA | deoxyribonucleic acid |
| E. coli | Escherichia coli |
| GSH | glutathione (reduced form) |
| GST | glutathione-S-transferase |
| LB | Luria-Bertani Broth |
| M | Molar |
| ORF | open reading frame |
| PCR | polymerase chain reaction |
| rEPF | recombinant Early Pregnancy Factor |
| RSP | reverse sequencing primer |
| SDS | sodium dodecyl sulphate |
| SDS-PAGE | sodium dodecyl sulphate-polyacrylamide gel electrophoresis |
| Tris | Tris(hydroxymethyl)aminomethane |
| USP | universal sequencing primer |

Cloning of Human cpn10 Open Reading Frame

Polymerase chain reaction (PCR) was used to initially amplify part of the ORF (274 bp) of the human cpn10 cDNA from a melanoma cell line A2058 cDNA lambda library (Stratagene). A degenerate cpn10 amplimer (P1) was designed from the amino acid sequence VLDDKDYFL (SEQ ID NO:1) corresponding to amino acid residues 83–91 of human cpn10. The primer P1 has the sequence 5' ARRAARTARTCYTTRTCRTC 3' (SEQ ID NO:2) where R is A or G and Y is C or T. The reverse sequencing primer (RSP) was used for PCR amplification (the non-specific primer) as well as for sequencing DNA constructs and has the sequence 5' CAGGAAACAGCTATGAC 3' (SEQ ID NO:3). The universal sequencing printer has the sequence 5' GTAAAACGACGGCCAGT 3' (SEQ ID NO:4). PCR amplification of the phage library was achieved using a non-specific upstream amplimer (RSP) and P1, each at 0.5 μM final concentration, 1.5 mM $MgCl_2$ (Pharmacia Biotech), 1 × polymerase buffer (Boehringer Mannheim) and 5 units of *Thermus aquaticus* DNA polymerase (Boehringer Mannheim) in a final volume of 50 μL. For 30 cycles, the parameters were: denaturation at 94° C. for 1 min. annealing at 40° C. for 30 sec and extension at 72° C for 3 min. A final extension at 72° C. for 7 min was followed by a soak cycle at 4° C. for 10 min. An aliquot of 1 μL was reamplified under the same conditions to increase the cop) number.

Two cpn10 specific amplimers encompassing the open reading frame were designed. The upstream primer P2, 5'-GCGCGGATCCATGGCAGGACAAGCGTTTAG-3' (SEQ ID NO:5) was designed from the sequence of the initial PCR fragment. The downstream primer P3, 5' ATATGAATTCAGTCTACGTACTTTCC-3' (SEQ ID NO:6) was designed from sequence obtained from the Expressed Sequence Tag database via ANGIS (Accession No. HUM00TB037). A 319 bp fragment was amplified from the phage library using the same reaction and cycling conditions as above except the annealing temperature was 50° C.

DNA Constructs and Analysis

Figure 4:
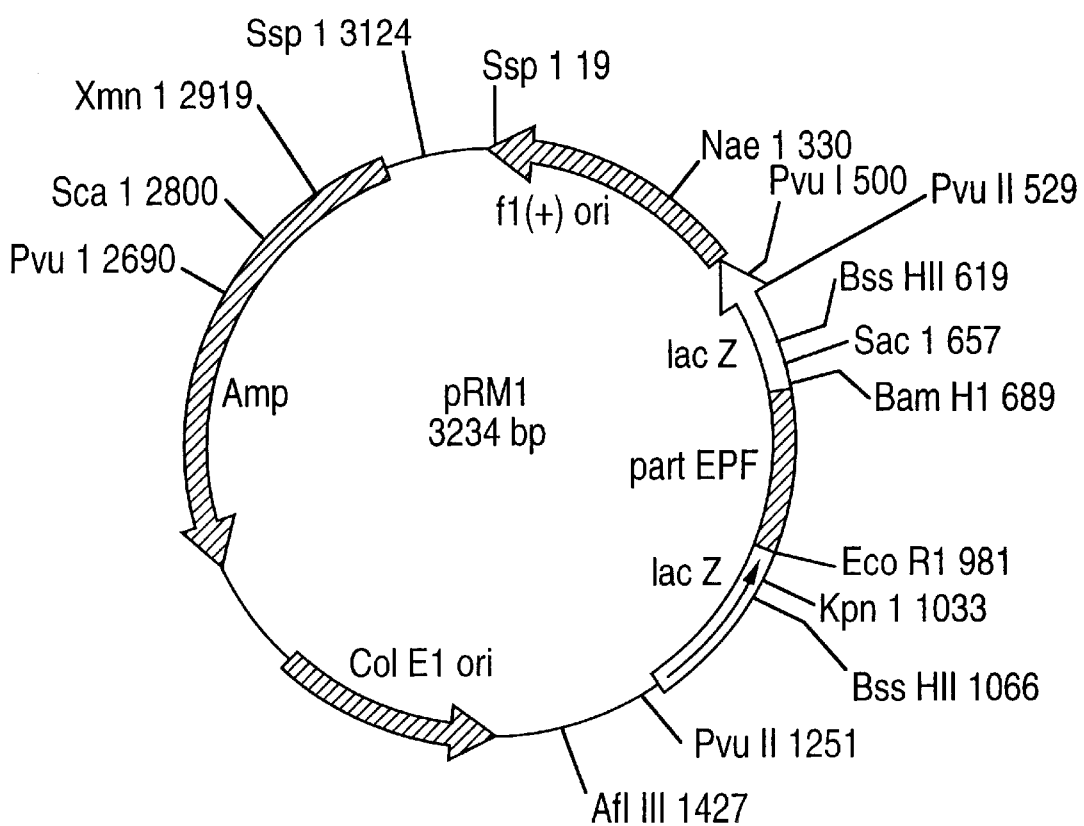
Figure 5:
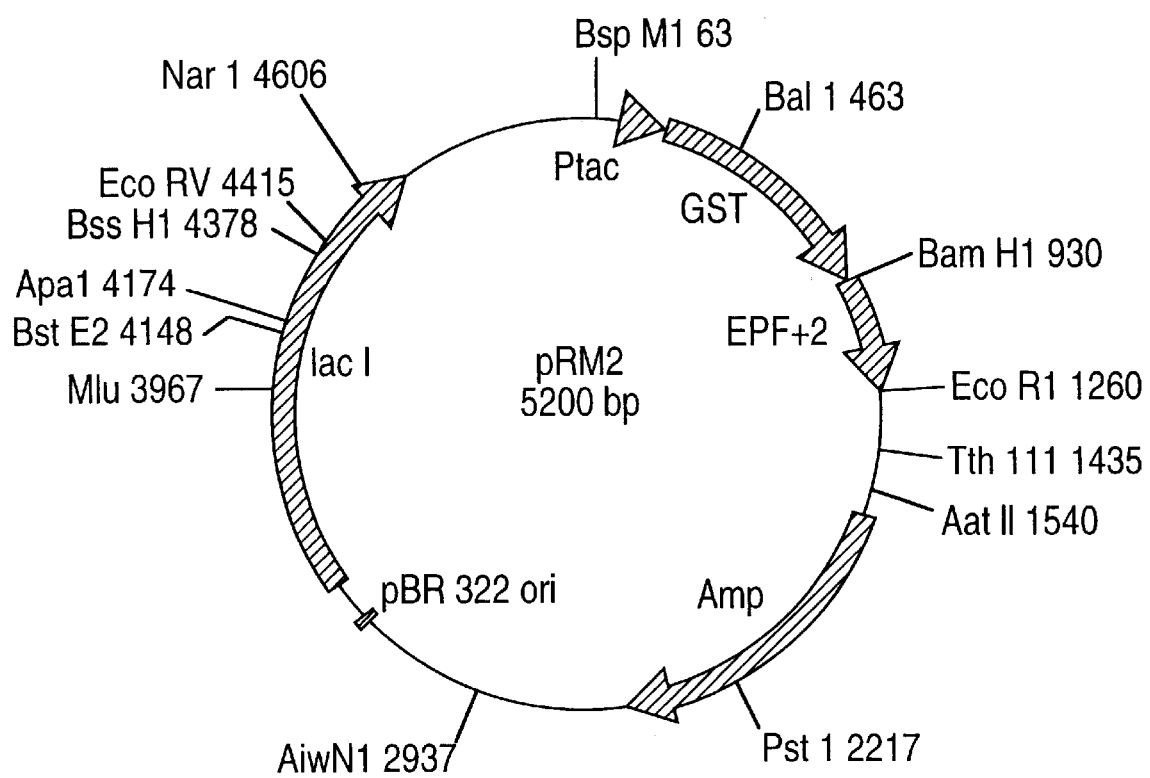
Figure 6:
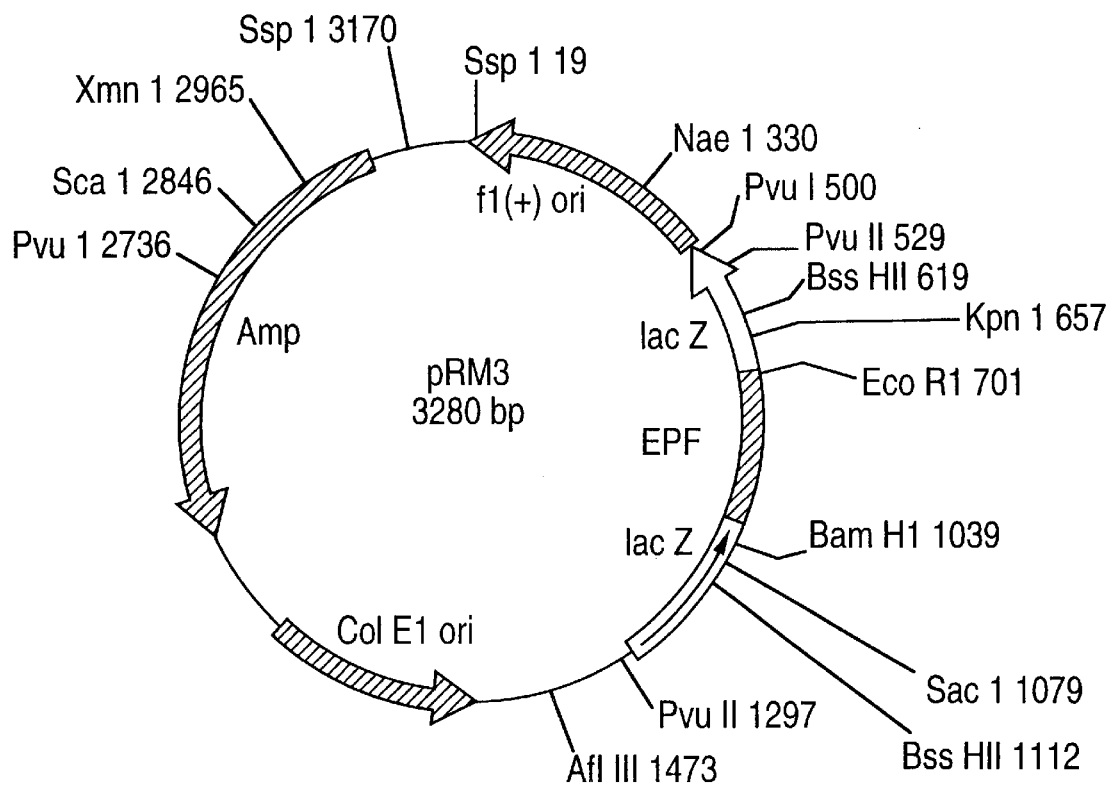

All restriction enzyme digests of PCR products and vectors were performed according to Sambrook et al. (Sambrook et al., 1989, Molecular Cloning: A Laboratory Manual. 2nd Ed. Cold Spring Harbor Press, Cold Spring Harbor, N.Y.) using restriction enzymes and their buffers obtained from Boehringer Mannheim. The initial PCR fragment was digested with Eco R1 and ligated (Sambrook et al., 1989, Molecular Cloning: A Laboratory Manual. 2nd Ed. Cold Spring Harbor Press, Cold Spring Harbor, N.Y.) into the Eco RI and Sina I sites of pBluescript KS(+) (Stratagene)

creating the plasmid pRMI (FIG. 4: partial cpn10 insert 274 bp). The 319 bp product was digested with Bam HI and ECo RI and initially cloned into the expression plasmid pGEX-2T (Pharmacia Biotech) creating the plasmid pRM2 (FIG. 5). To confirm its identity, the Bum HI-Eco R1 fragment was subcloned into pBluescript (SK+) (pRM3; FIG. 6) and sequenced. DNA was analysed on 0.8–1.0% (w/v) agarose gels containing ethidium bromide and after electrophoresis was viewed under UV illumination.

Transformation of *E. Coli*

Competent *E. coil* DH5α cells (100 μL) were transformed with the plasmids by the heat pulse method (Sambrook et al., 1989, Molecular Cloning: A Laboratory Manual. 2nd Ed. Cold Spring Harbor Press, Cold Spring Harbor, N.Y). The mixture of cells and DNA (10–100 ng) was placed on ice for 30 min and heat pulsed for exactly 2 min at 42° C. and placed back on ice for 2 min. The cells were allowed to recover at 37° C. with shaking for 1 hr after the addition of 0.9 mL of LB. A 100 μL aliquot was plated onto LB agar plates supplemented with Ampicillin at a final concentration of 100 μg/mL. After incubation overnight at 37° C. random colonies were selected for further investigation.

DNA Sequence Determination

Restriction fragments of the PCR products were cloned into pBluescript and sequenced in both orientations by the dideoxy chain-termination method using the T7 Polymerase Kit according to the manufacturer's instructions (Pharmacia Biotech). Approximately 2 μg of plasmid DNA was denatured, ethanol precipitated and annealed to either the USP, RSP or P3. The sequencing reactions were electrophoresed on a 8% acrylamide/46/% urea gel. After fixing and drying, X-ray film was exposed to the gel overnight and developed.

Expression and Purification of recombinant cpn10 *E. coli*

Clones transformed with pRM2 were screened for expression of the Glutathione-S-transferase fusion protein on a small culture scale (2 ml) according to methods described by Smith et al. (Smith et al., 1988, Gene 67 (1) 31–40). An overnight culture was diluted, induced to express the fusion protein by the addition of IPTG to 0. mM and grown at 37° C. for several hours. The cells were pelleted, lysed in PBS/0.1% Triton X-100 and the lysate mixed with 50% Glutathione-Agarose beads (Sigma Chemical Company). The recombinant fusion protein was eluted from the affinity beads by boiling in SDS loading buffer. An aliquot of the sample was run on a 10% SDS-PAGE gel. The gel was fixed and then stained with Coomassie blue. After confirming the expression of the fusion protein the purification of rcpn10 from the GST moiety was undertaken on a larger scale.

Cells were grown and induced as above, the cell pellet resuspended in PBS, sonicated (output level 4, 50% duty cycle, 2×30 sec) and the cell lysate stored at −30° C. Lysate from 10 liter cell culture was thawed and rcpn10 isolated by similar techniques to those used by Gearing et al. (Gearing et al., 1989, Biotechnology 7 1157–1161) for isolation of rLIF. Briefly, TRITON X-100, a non-ionic surfactant; was added to a final concentration of 0.1% and cellular debris removed by centrifugation (15 min, 15000 rpm, 4° C.). Ten ml glutathione-SEPHAROSE, cross linked agarose beads 4 gel (Pharmacia - LKB Biotechnlogy) was added to the supernatant and the slurry mixed for 2 hr, 4° C. The gel was pelleted, washed × 5 with 50 ml PBS/0.1% Triton X-100 once with 50 ml 0.05 M Tris-HCl pH 8.0/0.15 M NaCl and once with 0.05M Tris-HCl pH 8.0/0.15 M NaCl/2.5 mM CaCl$_2$. The gel was resuspended in 4 ml of 0.05 M Tris-HCl pH 8.0/0.15 M NaCl/2.5 mM CaCl$_2$ buffer, 1000 units thrombin (Sigma T6884) added and the slurry was mixed in a shaking waterbath for 1 hr, 37° C. The gel was pelleted, the supernatant retained, and the gel was then washed with 3×4 ml 0.05 M Tris-HCl pH 8.0/0.15 M NaCl. These washes and the first supernatant, which contain the rcpn10, were pooled, yielding 4–5 mg recombinant protein. Additional rcpn10, which was non-specifically bound to the gel, was recovered as follows. Four ml 0.05 M Tris-HCl pH 8.0/2 M NaCl was added and the slurry mixed for 2 hr, 4° C.

After pelleting, the gel was washed with 3×2 ml of this 0.05 M Tris-HCl pH 8.0/2 M NaCl buffer, the washes pooled with the first supernatant, yielding a further approximately 1 mg rcpn10. Protein concentrations were estimated by the method of Lowry et al. (Lowry et al., 1951, J. Biol. Chem. 193 265–275); proteins were analysed by SDS-PAGE using 15% Tris-Tricine gels (Schagger et al., 1987, Anal. Biochem. 166 368–379).

The recombinant cpn10 has two additional amino acids at the N terminus. The N terminus of the recombinant protein is Gly-Ser-Methionine-Ala whereas the N-terminus of native protein is Ac-Ala. The amino acid sequence of the recombinant cpn10 is as follows: GSMAGQAFRK-FLPLFDRVLVERSAAETVTKGGIML-PEKSQGKVLQATVVA VGSGSKGKGGEIQPVS-VKVGDKVLLPEYGGTKVVLDDKDYFLFRDGDILG-KYVD (SEQ ID NO:9)

2. Application of Mammalian cpn10 16

(a) Assay for cpn10

Antigen

A bacterial fusion protein, GST/cpn10, was expressed and isolated with glutathione-Sepharose, as described for preparation of cpn10. The fusion protein was eluted from the gel by application of 50 mM reduced glutathione in Tris-buffered saline. Eluted fractions were analysed by SDS-PAGE and those containing the most fusion protein were pooled. Protein concentration was determined by the method of Lowry et al., 1951, J. Biol. Chem. 193 265–275.

Antibody

Figure 7:
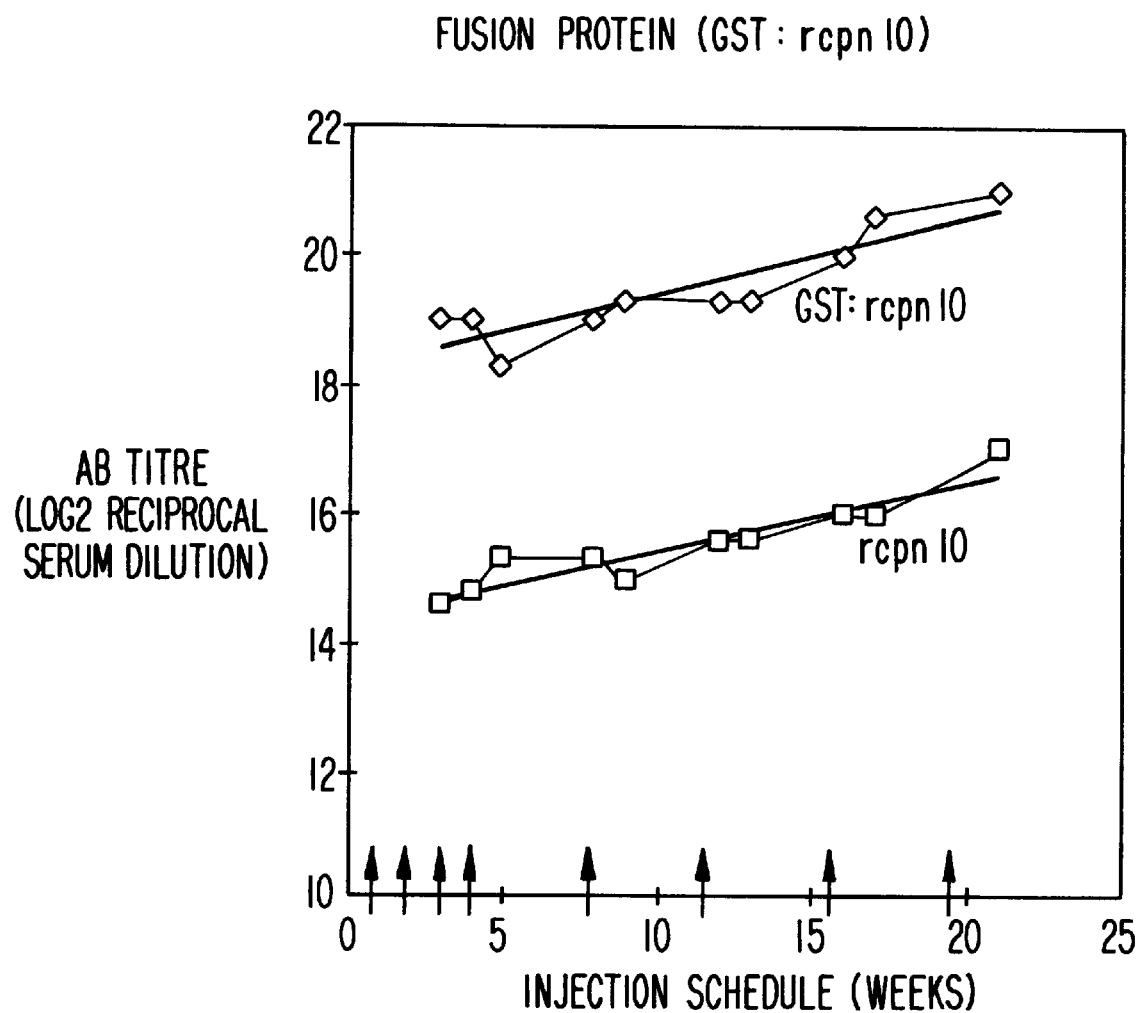
Figure 8:
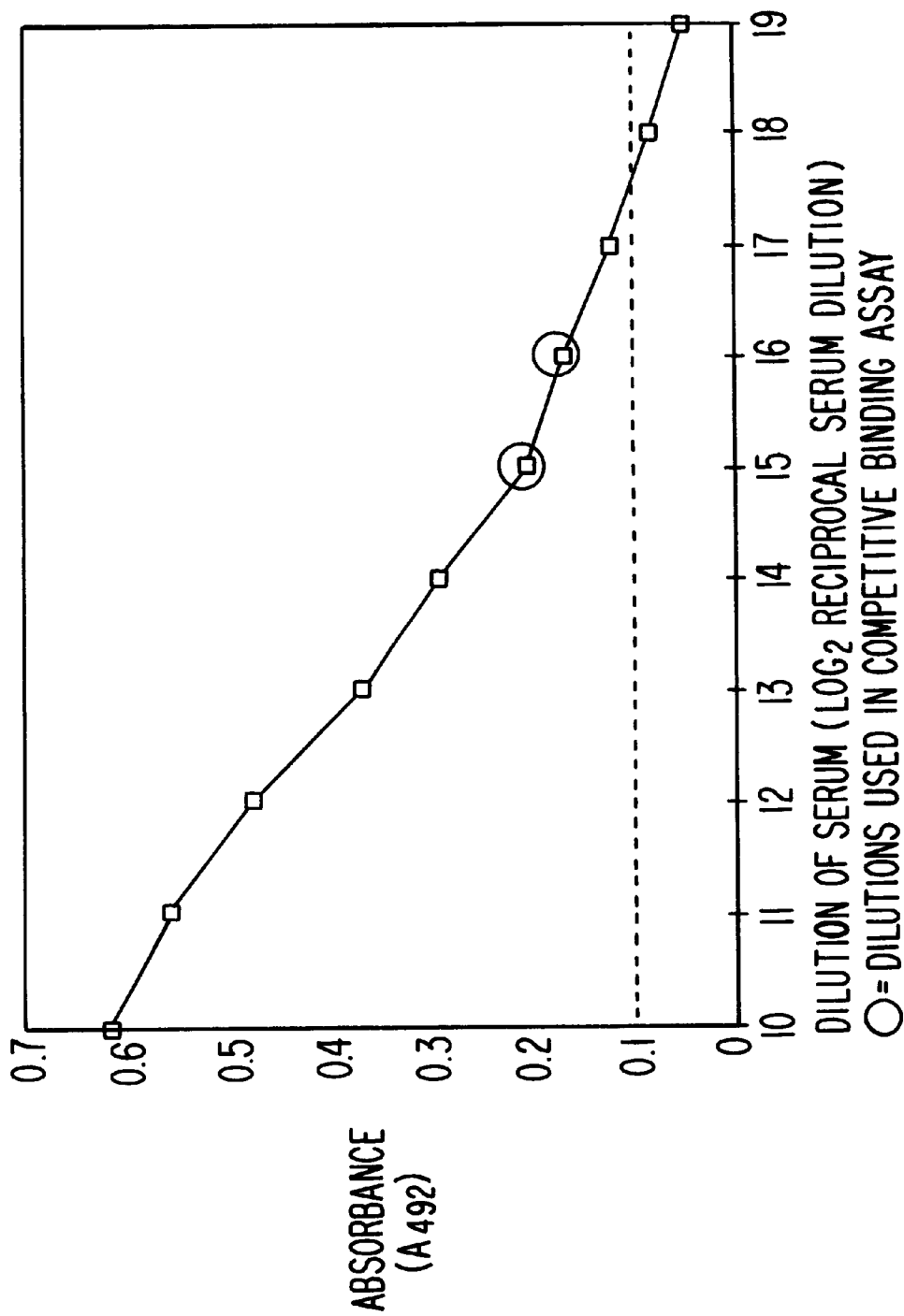

Antibodies against the fusion protein were raised in rabbits using an immunisation schedule consisting of 4× weekly injections followed by at least 4× monthly boosts. Approximately 10 pg protein, emulsified in Freund's Complete Adjuvant for the first injection and in Incomplete Adjuvant thereafter, was used for each injection. Rabbit serum was screened for anti-cpn10 antibodies by ELISA using plates coated initially with cpn10 (5 μg/ml) and a streptavidin-biotin detection system (Amersham). The antibody (Ab) titres against cpn10 and against the whole fusion protein (in this case GST/cpn10, 5 μg/ml, was bound to the plate) in serum of rabbit #42 are shown in FIG. 7. Titration of a serum sample against cpn10, taken from this rabbit after the 4th booster dose, is illustrated in FIG. 8.

Immunoassay

Figure 9:
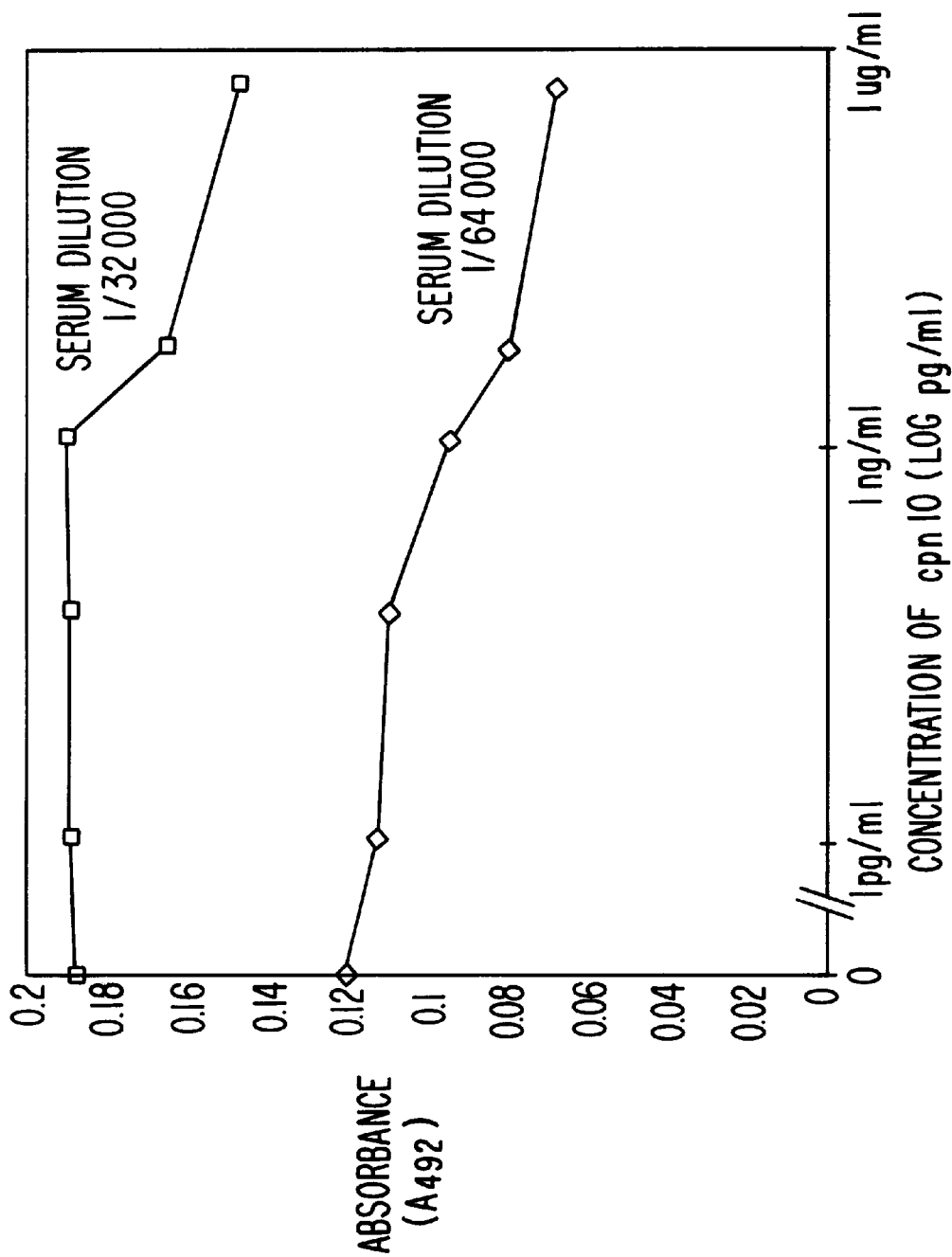
Figure 10:
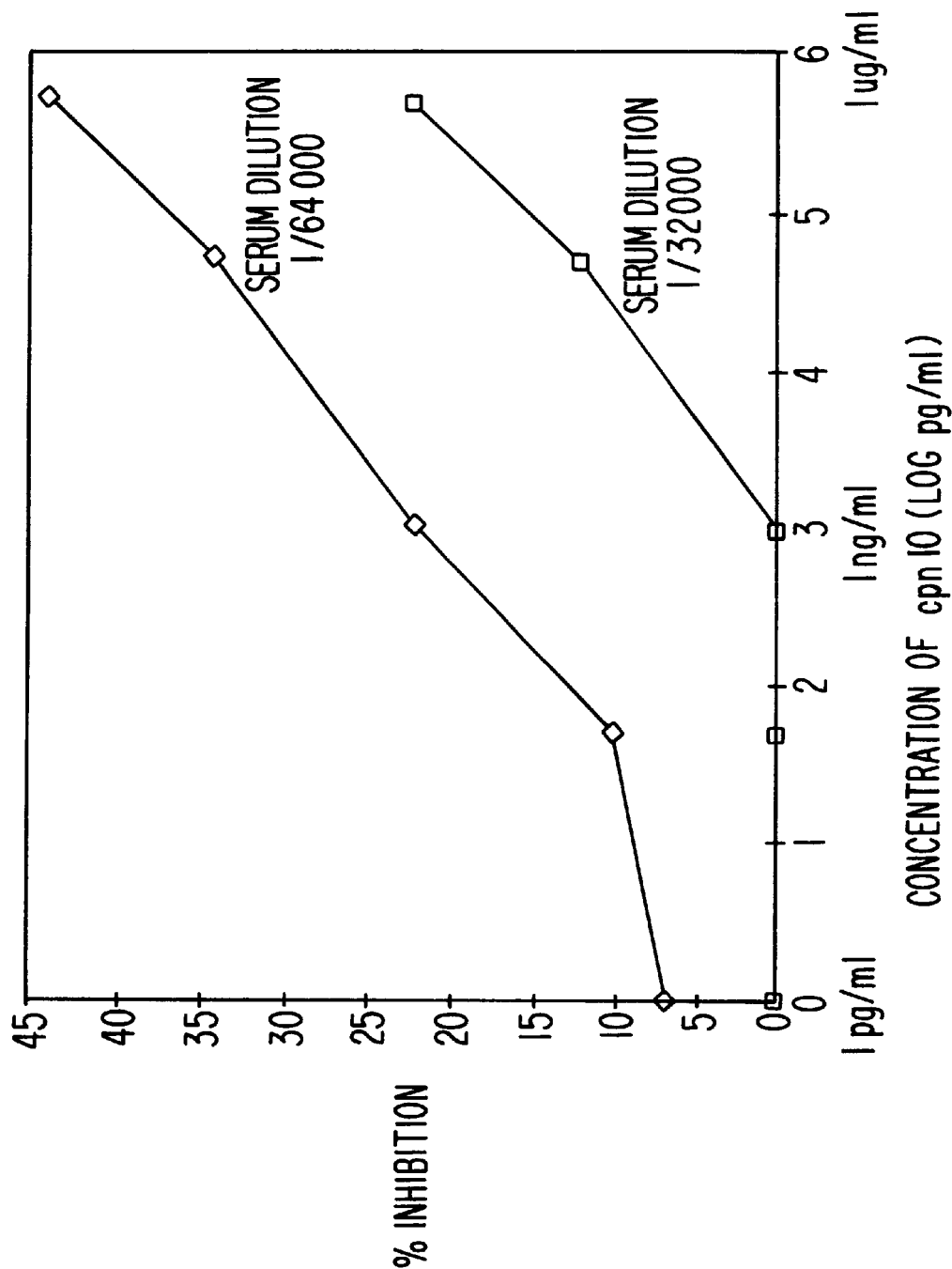

This antibody was then used in a competitive binding assay for detection of cpn10, performed as follows. Antiserum, diluted 1:32000 and 1:64000 (final dilution: diluent 50 mM sodium phosphate buffer, pH 7.4, containing 0.2% w/v zelatin) %was incubated, separately (overnight, 4° C.) with various concentrations of cpn10. These mixtures were then tested by ELISA as described above, in plates coated with 5 μg/ml cpn10, as illustrated in FIG. 9. Absorbance values for each antibody/cpn10 mixture are compared with values obtained for the same antibody dilution incubated without cpn10. The degree of inhibition of binding of antibody to the plate is proportional to the amount of cpn10 in the original antibody-cpn10 mixture; from this, a standard curve can be constructed, as shown in FIG. 10.

While rabbit #42 is not sensitive enough to detect the very low concentration of cpn10 present in serum, we have established techniques which can:

(1) produce an anti-cpn10 antibody which displays normal hyperimmunisation properties: thus with known techniques for enhancement of the immune response, an antibody with greater avidity could be produced, and (2) produce a response in a standard immunoassay technique.

With improved antibodies, application of known methods for enhancement of the detection system and pretreatment of serum to both concentrate and partially purify cpn10 (e.g. by application to $CI_{18}$ Sep-pak cartridge [Waters] and elution with 80% acetonitrile in Tris-buffered saline, or to immobilised cpn60 in the presence of ATP and elution with EDTA), this technique, alone or in combination with other immunoassay techniques, could be developed for detection of cpn10 in serum.

Sensitivity of the Rosette Inhibition Test, the EPF Bioassay

The rosette inhibition test is non-quantitative and cannot be used to determine the cpn10 concentration in serum with accuracy. The assay may be used semi-quantitatively by comparing the limiting dose of samples, i.e. the highest dilution of sample giving a position response in the bioassay. Caution must be exercised with this approach since other substances in complex biological fluids, themselves inactive in the bioassay, can influence the response of active materials.

We have determined that the bioassay can detect as little as 5 –50 $\mu$m/ml pure cpn10 (Cavanagh et a/l., 1994, Eur. J. Biochem. 202 551–560). Based on the observed limiting dose of serum from pregnant women (known inhibitory substances having been removed from early pregnancy serum) and tumour-bearing animals and individuals as well as from rats 24 hr post-partial hepatectomy, the cpn10 concentration of serum is likely to be in the range 0.1–100 pg/ml.

Treatment with cpn10

(a) Organ/Skin Grafts

The Effect of Recombinant cpn10 on The Survival of Allogenic Skin Grafts In Rats Skin grafting Skin grafts were exchanged between inbred Lewis and DA rats (~100 g) using the following protocol. Abdominal full thickness skin was sutured onto a similar sized defect created on the lateral thoracic region using standard techniques. A group of six rats were grafted in one session, with each rat receiving one autograft and one allograft. Two Lewis and 2 DA rats received daily × 2 injections of recombinant cpn10 and one Lewis and one DA received buffer, injected around the site of the grafts. Different groups received different doses of cpn10. Injections were continued for 14 days. The grafts were covered with Vaseline gauze, Melolin dressing, plastic wrap and Co-flex elastic bandage. After 7 days, the grafts were examined daily for signs of necrosis. The day of rejection was taken as that on which 50% of the transplanted skin had undergone necrotic degradation.

Life Span of cpn10 Activity In Serum Following Injection of Recombinant cpn10 into Mice Various doses of recombinant cpn10 (see FIG. 11) were injected i.p. into BALB/c mice (~20 g) and the mice bled at various times after administration, commencing at 15 minutes (zero time). Serum was tested for cpn10 activity in the rosette inhibition test (see Morton et al., 1987, Current Topics in Developmental Biology 23 73–92) with spleen cells from C57BL/6 mice. Mice receiving platelet cpn10 were tested in parallel. The half life of cpn10 activity in serum was determined.

Results

Figure 11:
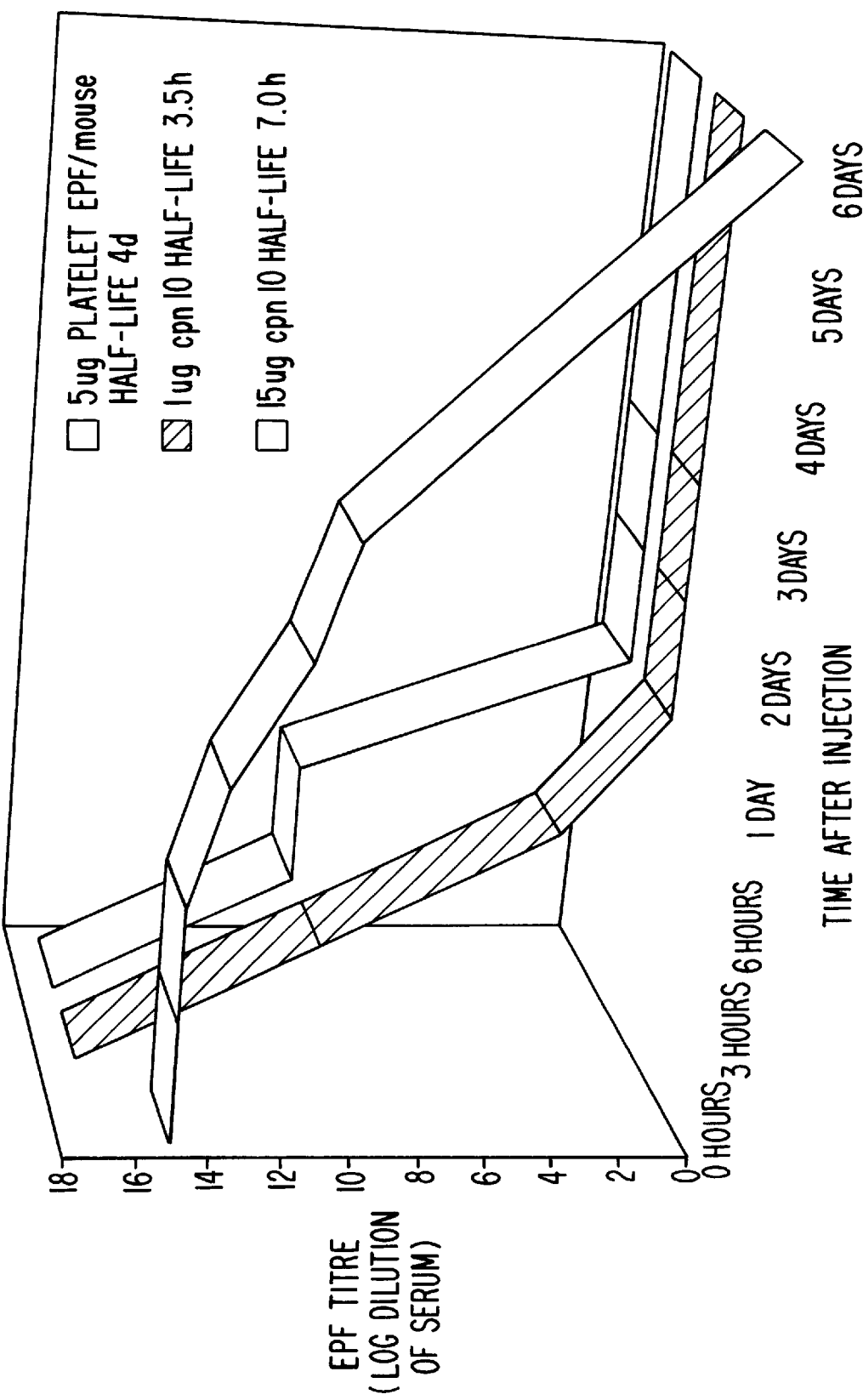

The results are shown in TABLE 2 and FIG. 11

There was a significant prolongation of graft survival time following injection of recombinant cpn10 ($p < 0.001$, Student's t test). The results showed a bell-shaped dose response curve, with the most effective doses being in the range of 2 to 20 $\mu$g cpn10×2/rat/day. The experiments in mice suggest that this recombinant cpn10 has a shorter than expected half life in serum, when compared with platelet cpn10; the half life of 1 $\mu$g and 15 $\mu$g recombinant cpn10 in serum of mice was only 3 hours and 7 hours respectively, compared with platelet cpn10 (5 $\mu$g), which had a half life of 4 days. However, these results have shown that cpn10 can significantly prolong the viability of allogenic skin grafts in rats. (See TABLE 2).

(b) Treatment of Mammals Including Humans With cpn10 To Promote Wound Healing

The Involvement of cpn10 In Tissue Repair

Growth factors are likely to be involved in the healing process, as their initial release from platelets is of fundamental importance in wound repair (Falange, 1993, J. Dermatol. Surg. Oncol. 19 716–720). Platelets have been shown to be a rich source of cpn10 (cpn10; Cavanagh et al., 1994, Eur. J. Biochem 222 551–560) and therefore may be one of the growth factors intimately involved in wound healing. Studies have been carried out to determine the effect of topically-applied recombinant cpn10 (rcpn10) on the healing of full-thickness skin defects created in mice.

Methods

Outbred, male Quackenbush mice (aged 8 weeks) were anaesthetized with Nembutal, shaved, skin sterilized with 70% v/v ethyl alcohol and a full thickness defect (8 mm diameter) created in the lateral thoracic region. One $\mu$g rcpn10 in 5 $\mu$l Tris-buffered 0.9% w/v sodium chloride (saline) pH 7.4, Tris-buffered saline alone (5 $\mu$l) or saline alone (5 $\mu$l) was applied directly to the wound, which was then covered with Vaseline gauze, Melolin non-adherent dressing and held in place with Co-flex elastic bandage. Twice daily, the mice were lightly anaesthetized with halothane (Fluothane, ICI), the dressings removed, 5 $\mu$l of the appropriate solution applied and the wound redressed. At various intervals, i.e. 24 hr, 48 hr, 3 d, 4 d, 5 d, 6 d and 7 d, groups of mice were euthanased with halothane, the would and surrounding tissue removed and the area of the wound measured.

Results

Figure 12:
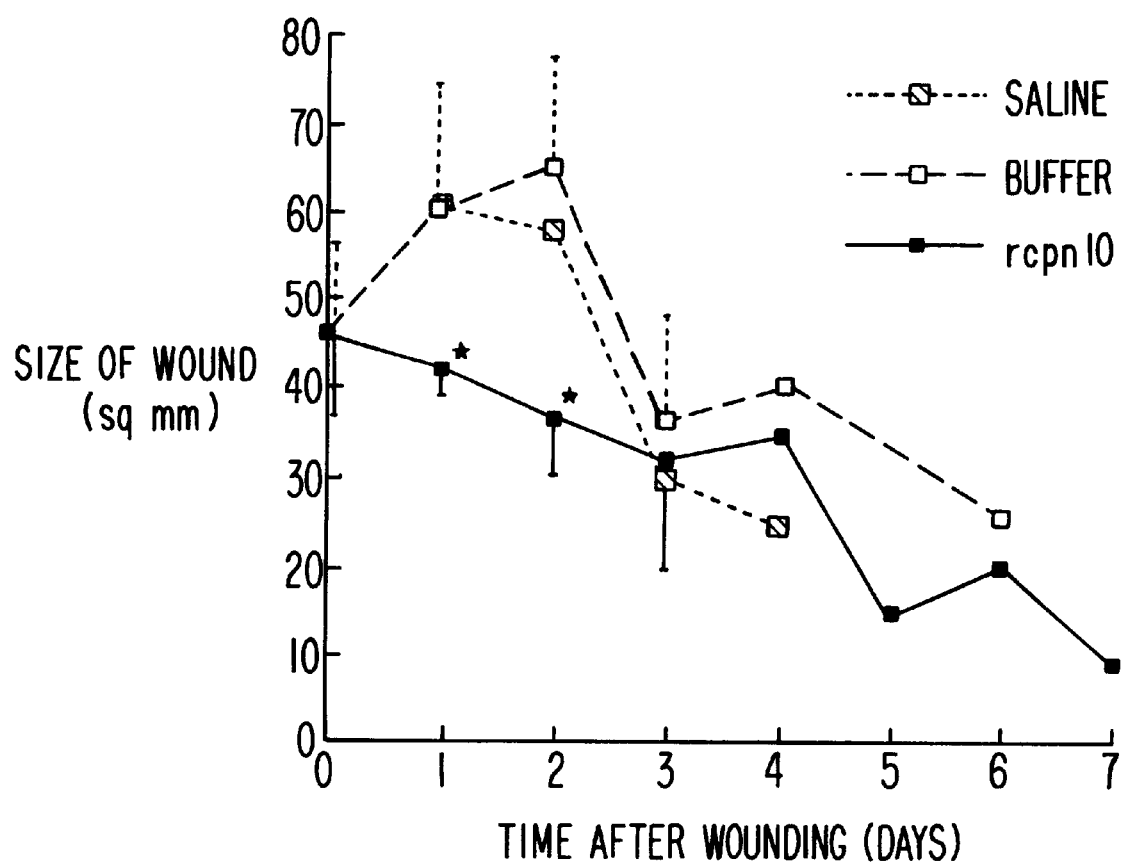

Following treatment with rcpn10, there was a significant accceleration of wound contraction, when compared with wounds treated with buffer or saline (FIG. 12). In the wounds treated with cpn10, wound contraction commenced within the first 24 hrs, whereas the control wounds, contraction commenced after 2 days (FIG. 12). From 3 days, there was no significant difference in wound size.

Conclusions

Cpn10 applied topically to full thickness wounds in mice, accelerates contraction and healing, with the process appearing to commence directly after wounding. Wound contraction in the control mice did not become evident until at least 48 hrs later.

Normally, wound healing takes place in three phases. Phase 1, the inflammatory phase (0–48 hrs), begins immediately after injury and is the time during which activated platelets secrete growth factors into the defect, facilitating fibroblast activation and increasing the activity of cells, e.g. macrophages, involved in the subsequent stages of wound healing. Phase 2, the proliferative phase (2–6 days), begins as the first fibroblasts appear and epidermal cells multiply and migrate to the wound site. Phase 3 is the maturation phase.

Wound contraction does not normally commence in phase 1, also known as the lag phase. During this phase, the shape and size of the excised wound is influenced by elastic forces in the neighbouring skin. These forces increase the initial size of the defect and give it a different shape corresponding to the tension lines present in the skin. As we have shown in the groups of mice treated with buffer or saline, the wounds were enlarged during the first 48 hrs. In contrast, the wounds in mice treated with rcpn10 contracted during this time suggesting that administration of rcpn10 directly to the wound accelerated migration of fibroblasts and deposition of collagen to the wound area. This finding will have enormous significance in the treatment of wounds including burns, as accelerated would contraction will greatly decrease fluid loss and risk of infection.

(c) Autoimmune Disease

The Effect of cpn10 On The Development of Experimental Allergic Encephalomyelitis In Rats, An Animal Model of Autoimmune Disease Introduction Experimental allergic encephalomyelitis (EAE) is an autoimmune demyelinating disease of the nervous system, induced by inoculation of animals with central nervous system myelin basic protein (MBP) in adjuvant, and widely studied as an animal model of multiple sclerosis (Raine, 1984, Laboratory Investigation 50 608–635). The clinical features of EAE in the rat, a commonly studied species, are dramatic overnight weight loss from day 10 after inoculation, followed by tail weakness and paralysis, hindlimb weakness and sometimes paralysis. Forelimb weakness and paralysis sometimes occur (Pender. 1986, Journal of Neurological Sciences 75 317–328). Experiments were undertaken to determine if administration of rcpn10 to rats following inoculation, would influence progress of the disease.

Methods

EAE Model

EAE was induced in inbred female Lewis rats (aged ~10 weeks) following inoculation with MBP in Freund's adjuvant into one footpad. Three groups of rats were included in the study. All were inoculated on day 0. Group 1 (n=4) received no treatment and animals were not handled during the incubation period of the disease (day 0 to day 8). Group 2 (Control group; n=5) received Tris-buffered saline (0.1 ml) i.p.×2 daily from day 0 to day 20. Group 3 (Test group; n=5) received 15 ug rcpn10 in Tris-buffered saline (0.1 ml) i.p.×2 daily from day 0 to day 20. From day 8, all rats were weighed and examined daily for 30 days.

(I) Tail weakness was graded as follows:-
   0=no weakness;
   1=weakness of distal part of the tail only, the distal tail failing to curl round the examiner's finger;
   2=weakness of the whole tail but the proximal tail still being able to be erected vertically against gravity:
   3=severe weakness with only a flicker of tail movement;
   4=complete flaccid paralysis of the tail.
(II) Hindlimb weakness was graded thus:
   0=no weakness;
   1=slight dragging of the toes of both hindfeet;
   2=severe dragging of both hindfeet but not of the rest of the hindlimbs;
   3=severe dragging of both hindlimbs, often with both hindlimbs displaced to one side of the body;
   4=total flaccid paralysis of the hindlimbs.
(III) The forelimbs were assessed in a similar way to the hindlimbs.

Total score was the sum of the scores in (I). (II) and (III).

Result

The time of onset of weight loss and period of maximum weight loss in the groups receiving no treatment or receiving injections of buffer alone (Control group) did not differ significantly (Table 3). However, initial weight loss was delayed in the group receiving cpn10 (Test group), compared with the group receiving no treatment, as also was the period of maximum weight loss (Table 3; $p<0.001$ $\chi^2$ distribution). There was no significant difference between the means of maximum weight loss in the three groups (Table 3).

Figure 13:
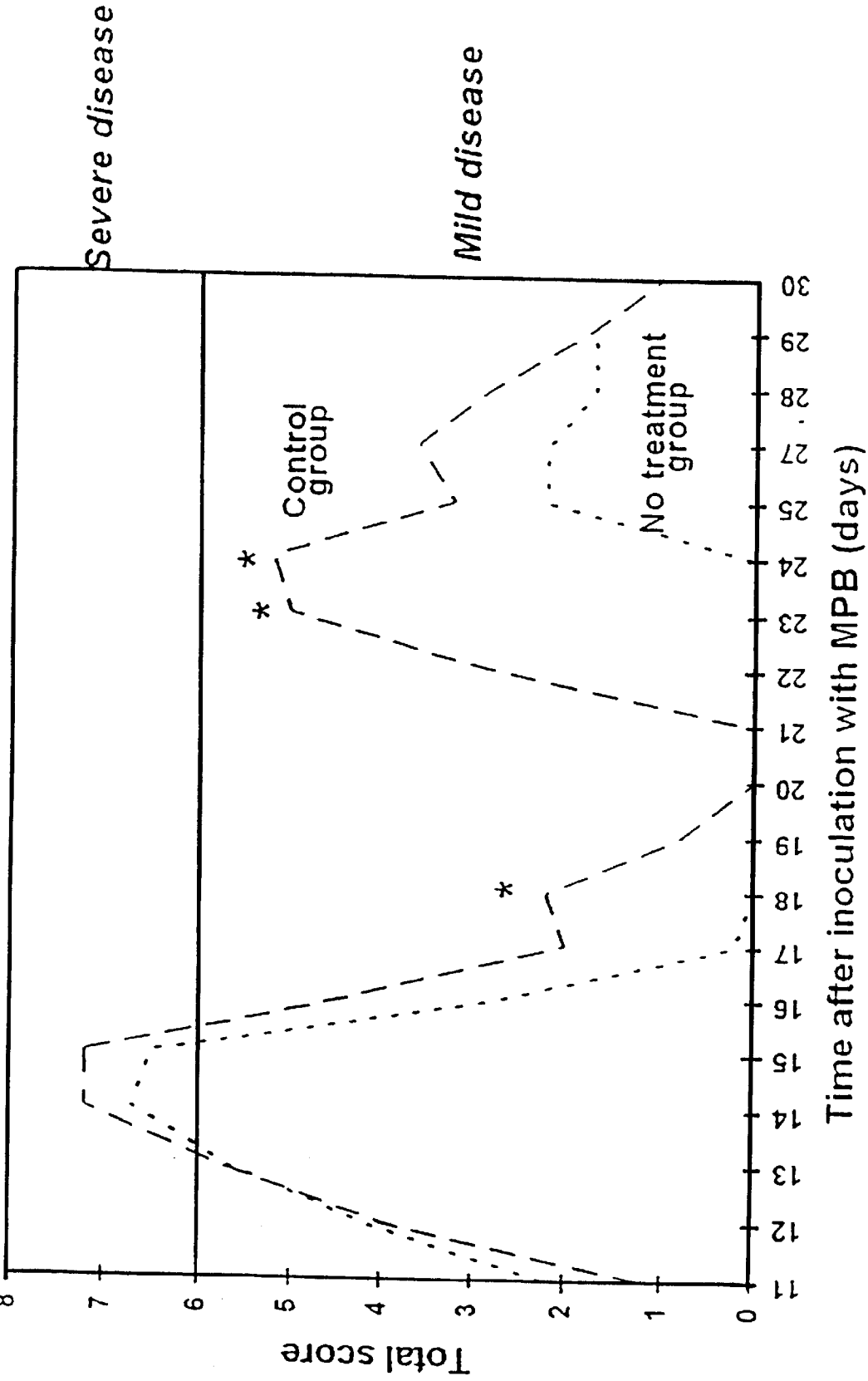

Administration of i.p. injections 2 × daily to the rats with the necessary handling involved did not affect the time of onset or the severity of the disease but did prolong the course of the disease for several days (day 17 to day 18 as shown in FIG. 13). However, one marked difference between these two groups was the recurrence of severe disease in the Control group at day 22, persisting until day 30. In the group receiving no treatment, mild disease only recurred in 3 rats on days 27 and 28.

Figure 14:
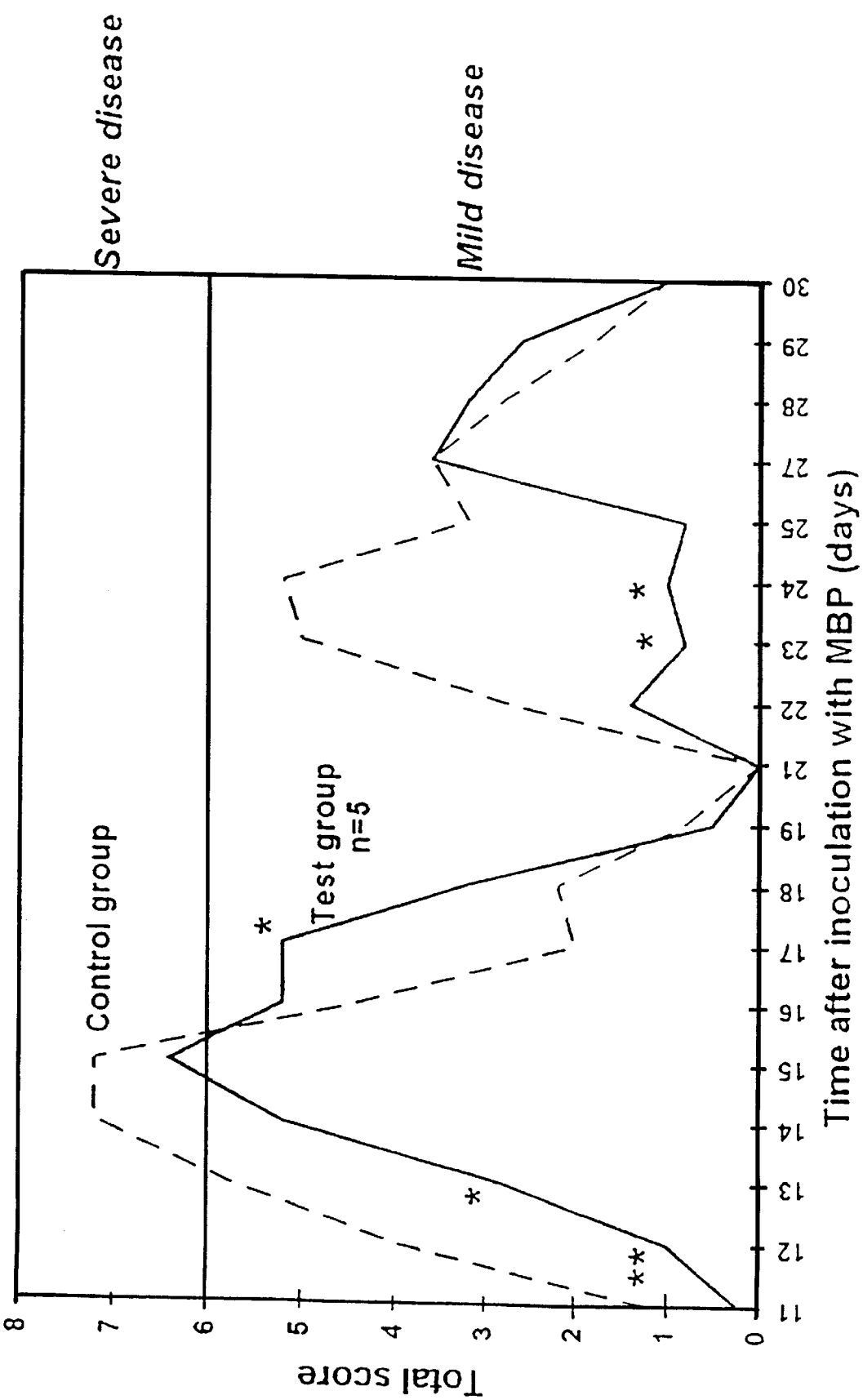
Figure 15:
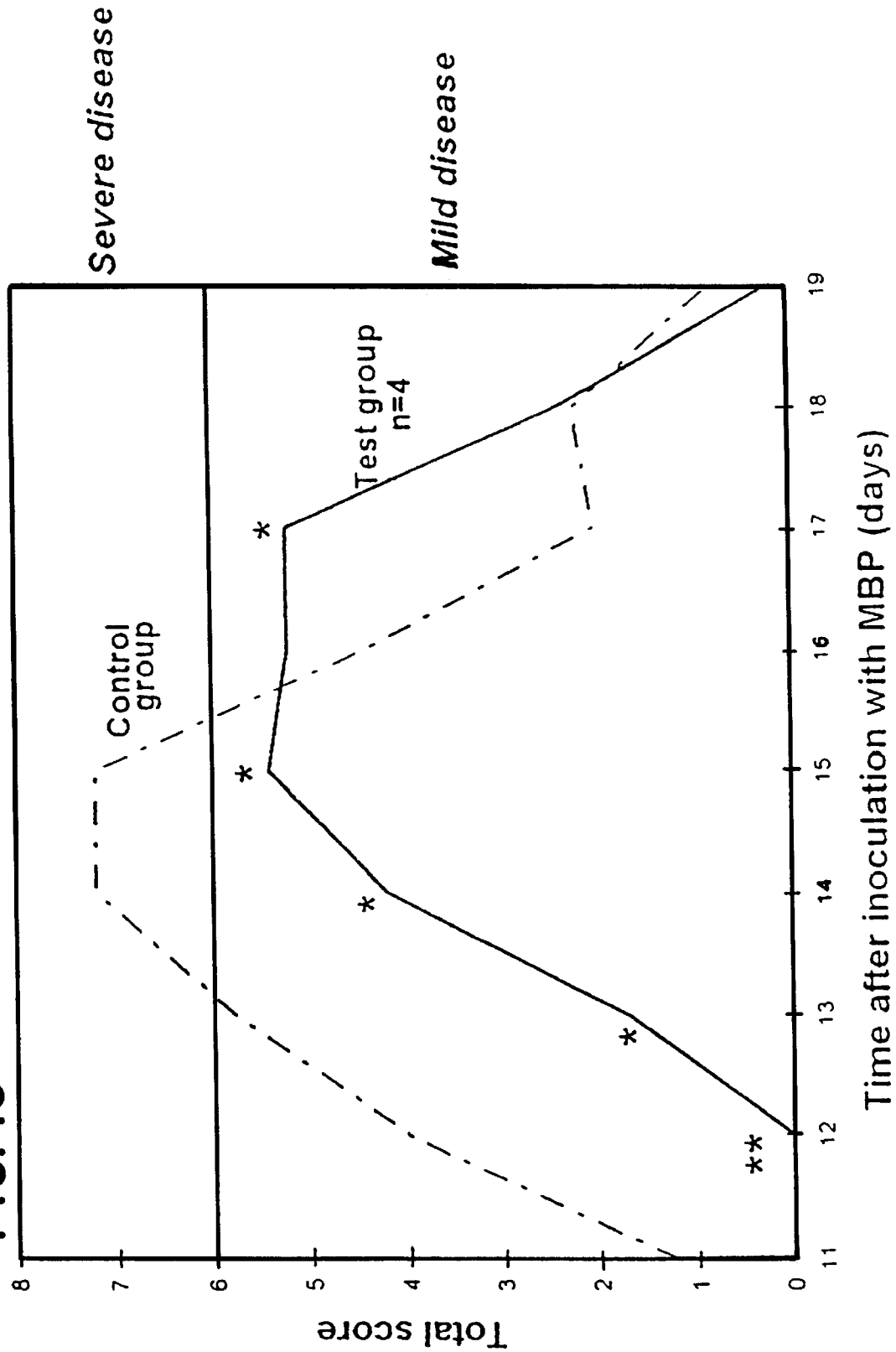

As with early weight loss, weakness and paralysis of the tail and limbs were delayed in the Test group, receiving rcpn10, compared with the Control group (FIG. 14: day 12, $p<0.01$: day 13, $p<0.05$, Heteroscedastic t test). In the Test group over the period from 14 to 16 days, only one rat developed severe disease, similar to that developed by the Control rats. The remaining 4 rats only developed mild disease during this period (FIG. 15, $p<0.95$, Heteroscedastic t test). Severe disease did not recur in the Test group, during the examination period; one rat developed mild disease at day 22 and the remaining rats from day 27 to day 30.

Conclusions

Treatment itself, i.e. administering fluid i.p.×2 daily to rats, did not effect the onset or severity of the disease but did marginally extend its time course. Furthermore, severe disease did recur during the observation period in the rats receiving daily injections of Tris-buffered saline but not in the rats receiving no treatment.

The most interesting observation made in the this study, was that treatment of the rats with cpn10 did significantly delay the onset and modify the clinical features of the disease in 4 out of 5 rats. It also prevented the recurrence of severe disease during the time these animals were under observation.

(d) Infertility and Miscarriage

A further aspect of the invention is the treatment of fertility and/or miscarriages with the administration of cpn10. This is of importance where the problem arises from the lack of cpn10. Experimental support below demonstrates the requirement for cpn10 during embryo development.

To create the situation of reduced cpn10 concentration, anti-cpn10 antibodies were developed and used. There is no animal model system available. It follows therefore from the experimental support that administration of cpn10 to increase the concentration of cpn10 during pregnancy will overcome the aforementioned problems of infertility and miscarriage.

Synthesis of cpn10 Derived Peptides

Peptides were synthesized to correspond with an N-terminal fragment (N-peptide i.e. Ac-AGQAFRKFLPLC) and an internal fragment (I-peptide i.e. EKSQGKVLQATC SEQ ID NO:8) of cpn10.

Conjugation of Peptides to Ovalbumin

Peptides were conjugated to ovalbumin by the heterobifunctional reagent SPDP, following manufacturer's instructions (Pharmacia-LKB Biotechnolkog, Uppsala, Sweden).

Immunisation Schedules

Adult outbred New Zealand rabbits were immunised with one of the conjugates in 4 × weekly injections followed by several monthly boosts.

For injection, the antigen was dialysed into 0.9% saline (Mr 12–15000 cut off dialysis tubing, Visking, Union Carbide, IL, USA) and emulsified with an equal volume of Freund's adjuvant (complete for the first injection, incomplete thereafter). Immunisations were via the s.c. route.

Screening of Anti-Serum

Antisera were tested in an ELISA against the relevant antigens (viz. I-peptide or N-peptide; ovalbumin) (5 mg/ml). Bound IgG was detected by the biotin-streptavidin system (Amersham) with o-phenylene diamine as substrate. Absorbance %%as read at 492 nm.

IgG was precipitated from anti-serum by 45% ammonium sulphate and the concentration determined by Lowry and gel electrophoresis. The IgG preparations were tested in an ELISA (Table 4) against the immunising peptide, conjugated to bovine serum albumin. The preparations were also tested for their ability to neutralise activity of mouse pregnancy serum in the rosette inhibition test. Various concentrations of antibody were incubated with an equal volume of serum, then the mixtures tested for activity in the rosette inhibition test. The lowest concentration of antibody that could completely neutralise activity was determined (see Cavanagh et al., 1994, Eur. J. Biochem. 222 551–560). Ten pg of anti-N-peptide Ab neutralised the activity of 1 ml pregnancy serum while 4 ng anti-I-peptide Ab was needed for complete neutralisation.

Passive Immunisation

Mature outbred male and female Quackenbush mice were caged in pairs at 7.30 a.m. and separated at 8.30 a.m. Female mice with vaginal plugs were injected with anti-N-peptide/ovalbumin, anti-I-peptide/ovalbumin or anti-ovalbumin lgG preparations at 9.00 a.m. and 5.00 p.m. on days 1 (day of mating) and 2 of pregnancy. The dose of specific IgG injected in the 2 dose regimen was estimated as approximately 1 mg/mouse/day. On day 7, mice were euthanased with $CO_2$, uteri examined for implanted embryos and the number of corpora lutea (CL) counted. In each group, the number of embryos/CL in the mice treated with the test IgG was compared with the number receiving the same dose of control IgG ($\chi^2$ test).

Results

The results, shown in Table 5 clearly demonstrate that neutralisation of cpn10 in pregnancy serum can adversely affect embryonic viability in the early stages of pregnancy. The ability of antibodies to neutralise activity in the rosette inhibition test is an in vitro monitor of their ability in vivo to adversely affect pregnancy.

Other Aspects of The Invention

In another aspect of the invention, further work has now elucidated two regions of the molecule with biological activity, corresponding with residues 1–11 and 34–44 in rat and human cpn10.

A peptide having the amino acid sequence Ac-AGQAFRKFLPL (SEQ ID NO:10) as well as a peptide having the sequence EKSQGKVLQAT (SEQ ID NO:11) have been found to be active in the rosette inhibition assay. Antibodies raised against both of these peptides are active as antagonists of cpn10 as described in detail in International Application PCT/AU94/00742 (WO95/15339). Both these peptides are prepared synthetically.

The invention therefore includes within its scope amino acid sequences: -
(i) AGQAFRKFLPL (SEQ ID NO:12);
(ii) Ac-AGQAFRKFLPL (SEQ ID NO:10) where Ac is acetyl;
(iii) EKSQGKVLQAT (SEQ ID NO:11) which may function as active centres of the cpn 10 molecule.

The invention also includes within its scope molecules (i), (ii) and (iii) having one or more end sequences $A_1$ and $A_2$ ie.
(iv) $A_1$AGQAFRKFLPLA$_2$;(SEQ ID NO:13)
(v) AGQAFRKFLPLA$_2$; (SEQ ID NO:14)
(vi) $A_1$AGQAFRKFLPL; (SEQ ID NO:15)
(vii) Ac-$A_1$AGQAFRKFLPLA$_2$; (SEQ ID NO:16)
(viii) Ac-AGQAFRKFLPLA$_2$; (SEQ ID NO:12)
(ix) Ac-$A_1$AGQAFRKFLPL; (SEQ ID NO:18)
(x) $A_1$EKSQGKVLQATA$_2$; (SEQ ID NO:19)
(xi) EKSQGKVLQATA$_2$; (SEQ ID NO:20)
(xii) AIEKSQGKVLQAT; (SEQ ID NO:21)
wherein $A_1$ and $A_2$ are amino acid sequences which may be added to one or each end of molecules (i) through (xii) and wherein Ac is acetyl.

In the above molecules (i) through (xii), it will be appreciated such molecules also include within their scope a single amino acid addition, deletion or substitution.

In regard to the use of cpn10 in regard to treatment of autoimmune disease, relevant diseases that may be treated by administration of cpn10 include insulin dependent diabetes mellitus, rheumatoid arthritis, systemic lupus erythematosis, Sjogren's syndrome, Graves disease and multiple sclerosis. This is evident from the relevant supporting data in regard to the EAE rat model provided herein.

In relation to the use of cpn10 in relation to treatment of organ transplants, skin grafts, the relevant supporting data given herein refers to the rat skin graft model described herein.

In relation to the use of cpn10 in relation to infertility treatment or prevention of miscarriage, the relevant supporting data refer to the effect of cpn10 antibody on embryonic development and implantation in mice.

In relation to the use of cpn10 in relation to wound healing and tissue repair or regeneration of tissue, this means that cpn10 can be used in treatment of burns, surgery, trauma, skin ulcers including bed sore and diabetic ulcers, infectious diseases involving tissue and organ damage (e.g. hepatitis), metabolic disease involving tissues and organ damage (e.g. liver cirrhosis) and degenerative disease involving tissue or organ damage. The support for these conclusions is given in the mouse wound model referred to herein and the liver regeneration data after partial hepactectomy in rats discussed in Quinn et al., 1994, Hepatology 20 No 5 1294–1302.

The data referred to herein also provides clear support for the use of cpn10 in treatment of inflammatory conditions including inflammatory bowel disease and infectious disease. Such data as described herein includes references drawn from the immunosuppressive effect of cpn10 in the rat EAE and skin graft models. This is also supported by Rolfe et al., 1983, Clin. exp. Immunol. 51 45–52 and Nature 278 No. 5705 649–651 showing that EPF can reduce delayed type hypersensitivity in mice.

The use of cpn10 in treatment of allergic disease including allergic rhinitis, asthma, atopic dermatitis, acute urticaria and drug hypersensitivity is also fully supported by the immunosuppressive effect of cpn10 in the rat EAE and skin graft models. This conclusion can also be drawn from Rolfe et al., 1983, Clin. exp. Immunol. 51 45–52 and Noonan et al., 1979, Nature 278 No. 5705 649–651 showing effect of EPF in reducing delayed type hypersensitivity in mice.

The use of cpn10 in relation to diagnosis of tumours and/or monitoring patients after surgical removal of tumours is supported by the reference Quinn et al., 1992, Cancer Immunol. Immunother. 34 265–271.

In regard to dosages that may be employed concerning administration of cpn10, a convenient dosage would be of the order of 1–1000 μg/kg of body weight and more preferably 50–200 μg/kg of body weight.

TABLE 1

| Sample | Limiting Dose (log reciprocal) | |
| --- | --- | --- |
| | Untreated | + 5/341 |
| Human platelet EPF (50 μg/ml) | 13 | <2 |
| Rat liver cpn 10 (50 μg/ml) | 13 | <2 |
| E. coli cpn 10 (groES) (50 μg/ml) | NA | NT |

TABLE 2

| TREATMENT | SKIN GRAFT SURVIVAL TIME | |
| --- | --- | --- |
| rEPF/cpn 10 (dose x 2/rat/day) | Lewis → DA Days ± SD (n) | DA → Lewis Days ± SD (N) |
| buffer alone | 8.7 ± 0.75 (7) | 9.1 ± 0.83 (8) |
| 1 μg | — | 9.0 ± 1.0 (3) (NS) |
| 5 μg | 14.0 ± 1.6 (4)* | 14.5 (2) |
| 20 μg | 15.2 ± 0.92 (4)* | 12.5 (2) |
| 70 μg | 10.0 (2) | 11.0 (2) |

TABLE 3

| Treatment Group | n | Onset of weight loss (day) | Max. period of weight loss (day) | p' | Max. weight loss (% wt. at d 10) | p* |
| --- | --- | --- | --- | --- | --- | --- |
| No treatment | 4 | 11 | 14–16 | | 15.4 | |
| Buffer (Control) | 5 | 11 | 15–17 | NS | 13.9 | NS |
| cpn 10 (Test) | 5 | 12–14 | 17–19 | p < 0.001 | 13.9 | NS |

TABLE 4

| Antibodies (mg/ml) | Titre (reciprocal serum dilution | |
| --- | --- | --- |
| | N-peptide (5 μg/ml) | I-peptide (5 μg/ml) |
| Anti-N-peptide | 128000 | <1000* |
| Anti-I-peptide | <1000* | 32000 |
| Anti-ovalbumin | <1000* | <1000* |

TABLE 5

| Antibody (total dose 2 mg/mouse) | No. of animals in group | Corpora lutea/mouse (mean ± sem) | Embryo/mouse (mean ± sem) | p* |
| --- | --- | --- | --- | --- |
| Anti-N-peptide-ovalbumin | 6 | 19.1 ± 1.2 | 10.6 ± 3.8 | < 0.05 |
| Anti-I-peptide-ovalbumin | 6 | 20.8 ± 0.8 | 17.1 ± 1.1 | < 0.02 |
| Anti-ovalbumin | 5 | 17.8 ± 1.0 | 16.8 ± 0.5 | NS |

TABLE LEGENDS

TABLE 1
Activity of cpn 10 in the rosette inhibition test
TABLE 2
Skin graft survival time.
p value when compared with control group receiving buffer alone
*p<0.001
TABLE 3
Time of Initial Weight Loss and Maximum Weight Loss in the Three Treatment Groups during the Course of EAE.
$\chi^2$ distribution
Student's t test
TABLE 4
Anti-N-peptide, anti-I-peptide and control anti-ovalbumin antibodies tested in an ELISA against N-peptide and I-peptide.
* 1 in 1000 was the lowest dilution tested.
TABLE 5
Effect of passive immunization of confirmed-mated mice at days 1 and 2 p.c., with antibodies to cpn10-derived peptides, on the number of of implanted embryos and corpora lutea present at day 7 p. c.
* (Heteroscedastic t-test).

We claim:

1. A process for promoting cell growth comprising the step of administering to a mammalian subject an amount of a recombinantly produced or synthetically produced mammalian chaperonin 10 (cpn10) in an amount effective to cause cell growth in said subject.

2. The process as claimed in claim 1 for enhancing tissue repair, wherein said mammalian subject is suffering from wounds or tissue damage.

3. The process as claimed in claim 1, wherein the mammalian subject is one to which organ or skin grafts have been applied.

4. The process as claimed in claim 1, wherein the mammalian subject is suffering from an inflammatory condition.

5. The process as claimed in claim 1, wherein the mammalian subject is suffering from an allergic disease.

6. The process as claimed in claim 1, wherein the mammalian subject is at risk of infertility or miscarriage.

7. The process according to claim 1, wherein said recombinantly produced or synthetically produced mammalian cpn10 has the amino acid sequence of SEQ ID NO:7.

8. A process for promoting immunosuppression comprising the step of administering to a mammalian subject an amount of a recombinantly produced or synthetically produced mammalian chaperonin 10 (cpn10) effective to achieve immunosuppression in said mammalian subject.

9. The process for immunosuppression according to claim 8, wherein said mammalian subject suffers from an autoimmune disease.

10. The process according to claim 9, wherein the autoimmune disease is selected from the group consisting of insulin dependent diabetes mellitus, rheumatoid arthritis, systemic lupus erythematosus, Sjorgen's syndrome, Graves disease and multiple sclerosis.

11. The process according to claim 8, wherein said recombinantly produced or synthetically produced mammalian cpn10 has the amino acid sequence of SEQ ID NO:7.

12. A process for promoting cell growth comprising the step of administering to a mammalian subject a recombinantly produced or synthetically produced peptide in an amount effective to cause cell growth in said mammalian subject, wherein said peptide is selected from the group consisting of
(i) a peptide of amino acid sequence AGQAFRKFLPL (SEQ ID NO:12);
(ii) A peptide of amino acid sequence Ac-AGQAFRKLPL (SEQ ID NO:10); and
(iii) a peptide of amino acid sequence EKSQGKVLAT (SEQ ID NO:11).

13. A process for promoting cell growth comprising the step of administering to a mammalian subject an amount of a recombinantly produced or synthetically produced mammalian chaperonin 10 (cpn10) peptide effective to achieve cell growth in said mammalian subject, wherein said peptide is selected from the group consisting of:
(i) a peptide of amino acid sequence AGQAFRKFLPL (SEQ ID NO:12) with a single amino acid deletion, addition or substitution;
(ii) a peptide of amino acid sequence Ac-AGQAFRKFLPL (SEQ ID NO:10) with a single amino acid deletion, addition or substitution; and
(iii) a peptide of amino acid sequence EKSQGKVLAT (SEQ ID NO:11) with a single amino acid deletion, addition or substitution.

14. A process for promoting immunosuppression comprising the step of administering to a mammalian subject an amount of a recombinantly produced or synthetically produced mammalian chaperonin 10 (cpn10) peptide effective to achieve immunosuppression in said mammalian subject, wherein said peptide is selected from the group consisting of:
(i) a peptide consisting of the amino acid sequence AGQAFRKFPLPL (SEQ ID NO:12);
(ii) a peptide consisting of the amino acid sequence Ac-AGQAFRKFLPL (SEQ ID NO:10) and
(iii) a peptide consisting of the amino acid sequence EKSQGVLAT (SEQ ID NO:11).

15. A process for promoting immunosuppression comprising the step of administering to a mammalian subject a recombinantly produced or synthetically produced peptide in an amount effective to cause or immunosuppression in said mammalian subject, wherein said peptide is selected from the group consisting of
(iv) a peptide of amino acid sequence AGQAFRKFLPL (SEQ ID NO:12) with a single amino acid deletion, addition or substitution;
(v) A peptide of amino acid sequence Ac-AGQAFRKLPL (SEQ ID NO:10) with a single amino acod deletion, addition or substitution; and
(vi) a peptide of amino acid sequence EKSQGKVLAT (SEQ ID NO:11) with a single amino acid deletion, addition or substitution.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 9 amino acids (B) TYPE: amino acid
        (C) STRANDEDNESS: single
        (D) TOPOLOGY: linear (xi) SEQUENCE DESCRIPTION: SEQ ID NO:1:

Val Leu Asp Asp Lys Asp Tyr Phe Leu
1               5

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

ARRAARTART CYTTRTCRTC                                           20

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:3:

CAGGAAACAG CTATGAC                                              17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

GTAAAACGAC GGCCAGT                                              17

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

GCGCGGATCC ATGGCAGGAC AAGCGTTTAG                                30

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

ATATGAATTC AGTCTACGTA CTTTCC                                    26

(2) INFORMATION FOR SEQ ID NO:7:

(i) SEQUENCE CHARACTERISTICS:
        (A) LENGTH: 104 amino acids (B) TYPE: amino acid
            (C) STRANDEDNESS: single
            (D) TOPOLOGY: linear (xi) SEQUENCE DESCRIPTION: SEQ ID NO:7:

Gly Ser Met Ala Gly Gln Ala Phe Arg Lys Phe Leu Pro Leu Phe Asp
1               5                   10                  15

Arg Val Leu Val Glu Arg Ser Ala Ala Glu Thr Val Thr Lys Gly Gly
                20                  25                  30

Ile Met Leu Pro Glu Lys Ser Gln Gly Lys Val Leu Gln Ala Thr Val
            35                  40                  45

Val Ala Val Gly Ser Gly Ser Lys Gly Lys Gly Gly Glu Ile Gln Pro
        50                  55                  60

Val Ser Val Lys Val Gly Asp Lys Val Leu Leu Pro Glu Tyr Gly Gly
65                  70                  75                  80

Thr Lys Val Val Leu Asp Asp Lys Asp Tyr Phe Leu Phe Arg Asp Gly
                85                  90                  95

Asp Ile Leu Gly Lys Tyr Val Asp
                100

(2) INFORMATION FOR SEQ ID NO:8:

(i) SEQUENCE CHARACTERISTICS:
            (A) LENGTH: 13 amino acids
            (B) TYPE: amino acid
            (C) STRANDEDNESS: single
            (D) TOPOLOGY: linear (xi) SEQUENCE DESCRIPTION: SEQ ID NO:8:

Xaa Ala Gly Gln Ala Phe Arg Lys Phe Leu Pro Leu Cys
1               5                   10

(2) INFORMATION FOR SEQ ID NO:9:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:9:

Glu Lys Ser Gln Gly Lys Val Leu Gln Ala Thr Cys
1               5                   10

(2) INFORMATION FOR SEQ ID NO:10:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:10:

Xaa Ala Gly Gln Ala Phe Arg Lys Phe Leu Pro Leu
1               5                   10

(2) INFORMATION FOR SEQ ID NO:11:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:11:

```
Glu Lys Ser Gln Gly Lys Val Leu Gln Ala Thr
1               5                   10
```

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:12:

```
Ala Gly Gln Ala Phe Arg Lys Phe Leu Pro Leu
1               5                   10
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:13:

```
Xaa Ala Gly Gln Ala Phe Arg Lys Phe Leu Pro Leu Xaa
1               5                   10
```

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:14:

```
Ala Gly Gln Ala Phe Arg Lys Phe Leu Pro Leu Xaa
1               5                   10
```

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:15:

```
Xaa Ala Gly Gln Ala Phe Arg Lys Phe Leu Pro Leu
1               5                   10
```

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:16:

```
Xaa Xaa Ala Gly Gln Ala Phe Arg Lys Phe Leu Pro Leu Xaa
1               5                   10
```

(2) INFORMATION FOR SEQ ID NO:17:

(i) SEQUENCE CHARACTERISTICS:
        (A) LENGTH: 13 amino acids

```
            (B) TYPE: amino acid
            (C) STRANDEDNESS: single
            (D) TOPOLOGY: linear (xi) SEQUENCE DESCRIPTION: SEQ ID NO:17:

Xaa Ala Gly Gln Ala Phe Arg Lys Phe Leu Pro Leu Xaa
1               5                   10

(2) INFORMATION FOR SEQ ID NO:18:

(i) SEQUENCE CHARACTERISTICS:
            (A) LENGTH: 13 amino acids
            (B) TYPE: amino acid
            (C) STRANDEDNESS: single
            (D) TOPOLOGY: linear (xi) SEQUENCE DESCRIPTION: SEQ ID NO:18:

Xaa Xaa Ala Gly Gln Ala Phe Arg Lys Phe Leu Pro Leu
1               5                   10

(2) INFORMATION FOR SEQ ID NO:19:

(i) SEQUENCE CHARACTERISTICS:
            (A) LENGTH: 13 amino acids
            (B) TYPE: amino acid
            (C) STRANDEDNESS: single
            (D) TOPOLOGY: linear (xi) SEQUENCE DESCRIPTION: SEQ ID NO:19:

Xaa Glu Lys Ser Gln Gly Lys Val Leu Gln Ala Thr Xaa
1               5                   10

(2) INFORMATION FOR SEQ ID NO:20:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:20:

Glu Lys Ser Gln Gly Lys Val Leu Gln Ala Thr Xaa
1               5                   10

(2) INFORMATION FOR SEQ ID NO:21:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:21:

Xaa Glu Lys Ser Gln Gly Lys Val Leu Gln Ala Thr
1               5                   10

(2) INFORMATION FOR SEQ ID NO:22:

(i) SEQUENCE CHARACTERISTICS:
            (A) LENGTH: 43 amino acids
            (B) TYPE: amino acid
            (C) STRANDEDNESS: single
            (D) TOPOLOGY: linear (xi) SEQUENCE DESCRIPTION: SEQ ID NO:22:

Lys Val Leu Xaa Ala Thr Val Val Ala Val Gly Ser Gly Ser Lys Glu
1               5                   10                  15
```

```
Tyr Gly Gly Thr Lys Val Val Xaa Xaa Xaa Xaa Asp Xaa Phe Leu Phe
             20                  25                  30

Arg Asp Gly Asp Ile Leu Gly Lys Tyr Val Asp
             35                  40
```

(2) INFORMATION FOR SEQ ID NO:23:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:23:

```
Lys Ser Gln Gly Lys Val Leu Gln Ala Thr Val Val Ala Val Gly Xaa
1                5                  10                  15

Gly Xaa Lys Val Leu Leu Pro Glu Tyr Gly Gly Thr
             20                  25
```

(2) INFORMATION FOR SEQ ID NO:24:

(i) SEQUENCE CHARACTERISTICS:
        (A) LENGTH: 47 amino acids
        (B) TYPE: amino acid
        (C) STRANDEDNESS: single
        (D) TOPOLOGY: linear (xi) SEQUENCE DESCRIPTION: SEQ ID NO:24:

```
Lys Phe Leu Pro Leu Phe Asp Arg Val Leu Val Glu Lys Gly Gly Ile
1                5                  10                  15

Met Leu Pro Glu Lys Xaa Gln Gly Lys Val Val Leu Asp Asp Lys Asp
             20                  25                  30

Tyr Phe Leu Phe Arg Asp Gly Asp Ile Leu Gly Lys Tyr Val Asp
             35                  40                  45
```

(2) INFORMATION FOR SEQ ID NO:25:

(i) SEQUENCE CHARACTERISTICS:
        (A) LENGTH: 102 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /product= "Other"
            /note= "The Xaa at position 1 is acetyl."

(xi) SEQUENCE DESCRIPTION: SEQ ID NO:25:

```
Xaa Ala Gln Ala Gly Phe Arg Lys Phe Leu Pro Leu Phe Asp Arg Val
1                5                  10                  15

Leu Val Glu Arg Ser Ala Ala Glu Thr Val Thr Lys Gly Gly Ile Met
             20                  25                  30

Pro Leu Glu Lys Ser Gln Gly Lys Val Leu Gln Ala Thr Val Val Ala
             35                  40                  45

Val Gly Ser Gly Gly Lys Gly Lys Gly Gly Glu Ile Gln Pro Val Xaa
             50                  55                  60

Xaa Lys Xaa Gly Xaa Xaa Val Leu Leu Pro Glu Tyr Gly Gly Thr Lys
65                   70                  75                  80
```

-continued

```
Val Val Leu Asp Asp Lys Asp Tyr Phe Leu Phe Arg Asp Gly Asp Ile
                 85                  90                  95

Leu Gly Lys Tyr Val Asp
                100
```